US009170190B2

(12) United States Patent
Goto et al.

(10) Patent No.: US 9,170,190 B2
(45) Date of Patent: Oct. 27, 2015

(54) SENSOR DEVICE AND IMAGE FORMING APPARATUS

(71) Applicants: Kazuma Goto, Miyagi (JP); Yoshihiro Oba, Miyagi (JP); Fumikazu Hoshi, Miyagi (JP); Toshihiro Ishii, Miyagi (JP); Satoru Sugawara, Miyagi (JP)

(72) Inventors: Kazuma Goto, Miyagi (JP); Yoshihiro Oba, Miyagi (JP); Fumikazu Hoshi, Miyagi (JP); Toshihiro Ishii, Miyagi (JP); Satoru Sugawara, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/326,564

(22) Filed: Jul. 9, 2014

(65) Prior Publication Data
US 2015/0015882 A1    Jan. 15, 2015

(30) Foreign Application Priority Data

Jul. 9, 2013   (JP) .................................. 2013-143136
Mar. 24, 2014  (JP) .................................. 2014-059385

(51) Int. Cl.
*G01J 4/00*    (2006.01)
*G01N 21/21*   (2006.01)
*G01N 21/86*   (2006.01)
*G03G 15/00*   (2006.01)
*G01N 21/47*   (2006.01)

(52) U.S. Cl.
CPC ............... *G01N 21/21* (2013.01); *G01N 21/86* (2013.01); *G03G 15/6591* (2013.01); *G03G 15/6594* (2013.01); *G01N 2021/217* (2013.01); *G01N 2021/4792* (2013.01); *G03G 15/50* (2013.01)

(58) Field of Classification Search
CPC .......................................................... G01J 4/00
USPC ....................................................... 356/364
See application file for complete search history.

(56) References Cited

U.S. PATENT DOCUMENTS 6,520,614 B2   2/2003  Kaneko
8,750,732 B2   6/2014  Ishii et al.
(Continued)

FOREIGN PATENT DOCUMENTS

JP   H10-160687   6/1998
JP   H11-249353   9/1999
(Continued)

OTHER PUBLICATIONS

U.S. Appl. No. 14/180,684, filed Feb. 14, 2014.
U.S. Appl. No. 14/199,056, filed Mar. 6, 2014.

*Primary Examiner* — Roy M Punnoose
(74) *Attorney, Agent, or Firm* — Cooper & Dunham LLP

(57) ABSTRACT

A sensor device is disclosed, including a database, and a processing apparatus. The database includes, for multiple different first types of objects, a first output data which are output data of an optical system acquired beforehand for each of the first objects in a case in which a surface of one side of the first object is set as the detection surface; and a second output data which are output data of the optical detection system acquired beforehand for each of the first objects in a case in which a surface of an other side opposite to the one side of the first object is set as the detection surface. The processing apparatus matches measurement data with the database, the measurement data being the output data of the optical detection system which is acquired with respect to a second object, and determines a type of the second object.

12 Claims, 28 Drawing Sheets

(56) References Cited

U.S. PATENT DOCUMENTS

| | | |
|---|---|---|
| 2012/0134693 A1 | 5/2012 | Hoshi et al. |
| 2013/0194573 A1* | 8/2013 | Ohba et al. .................... 356/369 |
| 2013/0216245 A1 | 8/2013 | Hoshi et al. |
| 2013/0216246 A1 | 8/2013 | Hoshi et al. |
| 2013/0216247 A1 | 8/2013 | Oba et al. |
| 2013/0228674 A1 | 9/2013 | Oba et al. |
| 2013/0235377 A1 | 9/2013 | Ishii et al. |

FOREIGN PATENT DOCUMENTS

| | | |
|---|---|---|
| JP | 2005-156380 | 6/2005 |
| JP | 3667183 | 7/2005 |
| JP | 2006-062842 | 3/2006 |
| JP | 2006-219281 | 8/2006 |
| JP | 2012-127937 | 7/2012 |

* cited by examiner

FRONT FACE PLAIN REFLECTED LIGHT

M
RECORDING PAPER

SURFACE DIFFUSION REFLECTED LIGHT

M
RECORDING PAPER

INTERNAL REFLECTION LIGHT

M
RECORDING PAPER

FIG.13

T13 OUTPUT LEVEL DATA

| BRAND | S1T | S2T | S3T | S1B | S2B | S3B |
|-------|-----|-----|-----|-----|-----|-----|
| A | ... | ... | ... | ... | ... | ... |
| B | ... | ... | ... | ... | ... | ... |
| C | ... | ... | ... | ... | ... | ... |
| D | ... | ... | ... | ... | ... | ... |

13-1 FIRST OUTPUT DATA 13-2 SECOND OUTPUT DATA (PLAIN REFLECTED LIGHT)

(DIFFUSION REFLECTED LIGHT)

FIG.26

| BRAND | S1T | S2T | S3T | S4T | S1B | S2B | S3B | S4B |
|---|---|---|---|---|---|---|---|---|
| A | ⋮ | ⋮ | ⋮ | ⋮ | ⋮ | ⋮ | ⋮ | ⋮ |
| B | ⋮ | ⋮ | ⋮ | ⋮ | ⋮ | ⋮ | ⋮ | ⋮ |
| C | ⋮ | ⋮ | ⋮ | ⋮ | ⋮ | ⋮ | ⋮ | ⋮ |
| D | ⋮ | ⋮ | ⋮ | ⋮ | ⋮ | ⋮ | ⋮ | ⋮ |

T26 OUTPUT LEVEL DATA 26-1 FIRST OUTPUT DATA 26-2 SECOND OUTPUT DATA

SENSOR DEVICE AND IMAGE FORMING APPARATUS

BACKGROUND OF THE INVENTION

1. Field of the Invention

The present invention is related to a sensor device and an image forming apparatus, and more particularly to the sensor device having an optical detection system, and the image forming apparatus including the sensor device.

2. Description of the Related Art

An image forming apparatus such as a digital copier, a laser printer, or the like transfers a toner image onto a surface of a recording medium represented by a printing paper, and fixes an image by heating and pressing with a predetermined condition, to form the image. An image forming condition is considered such as a phenomenon condition, a transfer condition, a fixing condition, and the like for an image formation. Especially, in order to perform a higher quality image formation, it is required to set the image formation conditions individually depending on a recording medium.

This is because the image quality in the recording medium is greatly influenced by a quality of material, thickness, humidity, smoothness, coating states, and the like. For example, regarding the smoothness, a fixation rate of toner becomes lower for concave portions in an irregularity of the printing paper surface depending on a fixing condition. Therefore, in a case in which fixing is not performed with a proper condition corresponding to the recording medium, uneven coloring occurs.

Moreover, with progress of recent imaging devices and diversification of expression methods, there are more than several hundred types of the recording media only for printing paper. Furthermore, there is a wide variety of brands with differences in specifications such as basis weight or the thickness in each type. For the high quality image formation, it is necessary to set a detailed imaging condition depending on each one of these brands.

Also, recently, brands have increased regarding a plain paper; a coated paper represented by a gloss coated paper, a matte coated paper, and an art coated paper; a plastic sheet; and a special paper where an embossing process is performed on a surface.

In a current image forming apparatus, in a case of filling trays with paper, a user needs to set the brand of a paper and a print condition for each of the trays. Thus, there is an inconvenience for setting. The user is required to have knowledge for distinguishing the type of the paper. If a wrong setting is performed, the most suitable image is not acquired. Also, in a case in which the brand of the paper to use is unknown, it is difficult to determine which brand is to be set for the paper.

An optical method is known to emit light on a recording medium, to receive reflected light and transmission light, and to detect the brand and a surface state of the recording medium.

For example, Patent Document 1 discloses a recording material differentiation apparatus for determining the type of a recording material by using the reflected light and the transmission light.

Also, Patent Document 2 discloses a sheet material quality differentiating apparatus for differentiating material quality of a sheet material based on an amount of reflected light which is reflected at a surface of the sheet material and an amount of transmission light which is transmitted to the sheet material.

Also, Patent Document 3 discloses an image forming apparatus which includes a reflection type optical sensor for identifying the type of the recording material being accommodated in a paper feeding, an identification part for identifying presence or absence of the recording material being accommodated in the paper feeding and presence or absence of the paper feeding based on a detection output from the reflection type optical sensor.

Also, Patent Document 4 discloses an image forming apparatus which includes a state detection part for detecting multiple polarization elements of the reflected light by irradiating light to the recording medium, a high pressure supply part for supplying a high pressure output value to perform the image formation, and an output controller for controlling the high pressure output value of the high pressure supply part based on a detection result of the multiple polarization elements by the state detection part.

Also, Patent Document 5 discloses an optical sensor which includes an irradiation system for irradiating linear polarization light in a first polarization direction to a sheet-like object, a first light detection system which is arranged on a light path of light which is irradiated from the irradiation system and is reflected through specular reflection at an object, an optical element through which the linear polarization component is transmitted in a second polarization direction perpendicular to the first polarization direction of the light which is reflected through diffusion reflection at the object, and a second light detection part for receiving light transmitting through the optical element.

Also, Patent Document 6 discloses a printing apparatus which includes an information acquisition part for acquiring two sets of information corresponding to both front side and back side of a print medium being an object to print, and a determination part for determining a type of a print medium based on the two sets of information acquired by the information acquisition part, in which the information part acquires information of an image pattern which is obtained by imaging a configuration state of fiber of a surface of the print medium.

Also, Patent Document 7 discloses an apparatus for identifying a type of a recording medium, which includes a detection part having a set of a light emission part and a light reception part, and a recording medium conveying part, in which while fixing a location of the detection part, types of a first surface of the recording medium and a second surface being an opposite side of the first surface are identified by moving the recording medium by the recording medium conveying part.

However, it is difficult for the above described technologies to determine the type of the object at higher precision with a simple configuration.

PATENT DOCUMENT

Patent Document 1: Japanese Laid-open Patent Publication No. 2005-156380
Patent Document 2: Japanese Laid-open Patent Publication No. H10-160687
Patent Document 3: Japanese Laid-open Patent Publication No. 2006-062842
Patent Document 4: Japanese Laid-open Patent Publication No. H11-249353
Patent Document 5: Japanese Laid-open Patent Publication No. 2012-127937
Patent Document 6: Japanese Patent No. 3667183
Patent Document 7: Japanese Laid-open Patent Publication No. 2006-219281

SUMMARY OF THE INVENTION

The present invention solves or reduces one or more of the above problems.

In one aspect of this disclosure, there is provided a sensor device including: a light source which emits light of a linear polarization having a first polarization direction toward a detection surface of an object; an optical detection system including an optical element which is arranged on a first light path of the light undergoing a diffusion reflection at the object in an incident surface with respect to the detection surface of the light emitted from the light source, and which transmits a linear polarization component of a second polarization direction orthogonal to the first polarization direction, a first optical detector which is arranged on a second light path of the light undergoing a regular reflection; and a second optical detector which receives the light passing through the optical element; a database including, with respect to multiple different types of first objects, a first output data which are output data of the optical system acquired beforehand for each of the first objects in a case in which a surface of one side of the first object is set as the detection surface; and a second output data which are output data of the optical detection system acquired beforehand for each of the first objects in a case in which a surface of an other side opposite to the one side of the first object is set as the detection surface; and a processing apparatus configured to match measurement data with the database, the measurement data being the output data of the optical detection system which is acquired with respect to a second object, and to determine a type of the second object.

Additional objects and advantages of the embodiments will be set forth in part in the description which follows, and in part will be obvious from the description, or may be learned by practice of the invention.

It is to be understood that both the foregoing general description and the following detailed description are exemplary and explanatory only and are not restrictive of the invention as claimed.

BRIEF DESCRIPTION OF THE DRAWINGS

Other objects and further features of embodiments will be apparent from the following detailed description when read in conjunction with the accompanying drawings, in which:

FIG. 5C is a diagram for explaining an internal reflected light;

FIG. 13 is a diagram of output level data by brand;

FIG. 26 is a diagram for explaining an output level data by brand for a third variation of the optical sensor;

DESCRIPTION OF THE PREFERRED EMBODIMENTS

Figure 1:
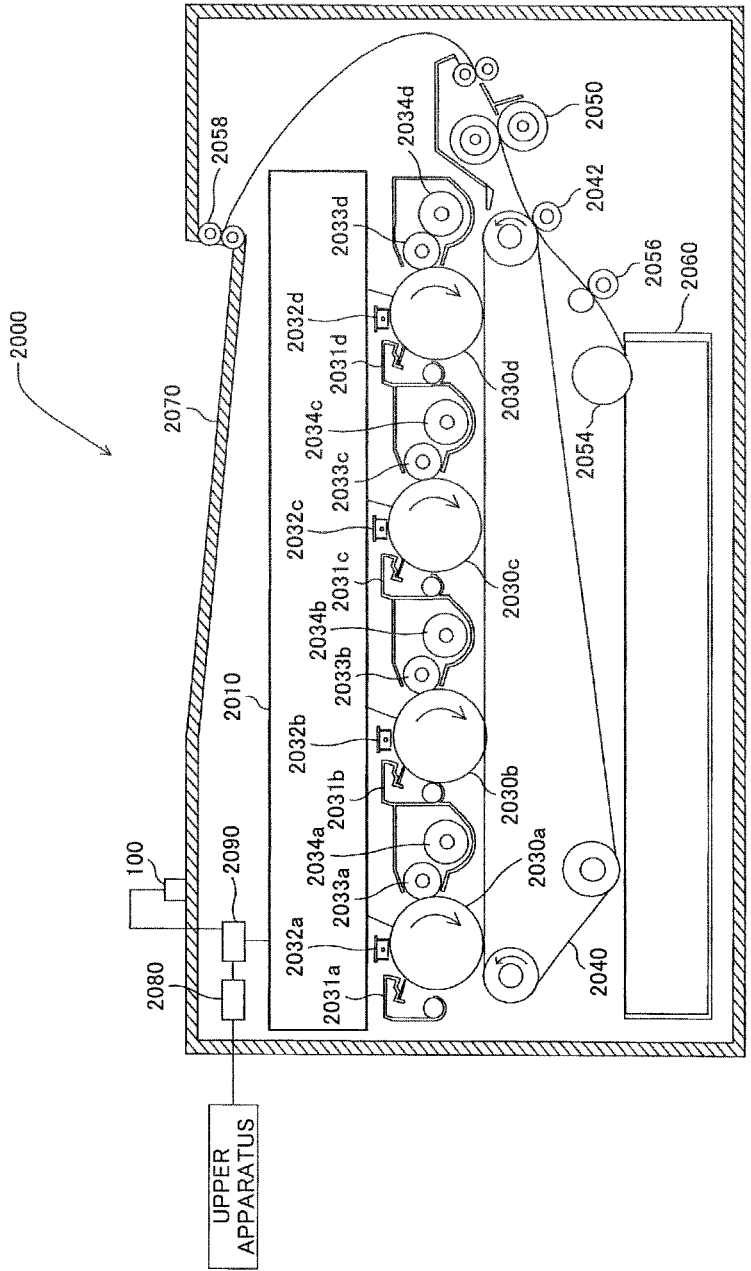
FIG. 1 is a diagram for explaining a general configuration of a color printer according to an embodiment.

Preferred embodiments are described below, with reference to FIG. 1 through FIG. 17A and FIG. 17B. In FIG. 1, a configuration of a color printer 2000 according to an embodiment is schematically illustrated.

The color printer 2000 is a tandem type multi-color printer which forms a full color image on a recording medium by overlaying four colors (black, cyan, magenta, and yellow), and includes a sensor device 100, an optical scanner 2010, four photosensitive drums 2030a, 2030b, 2030c, and 2030d (collectively called "photosensitive drums 2030"), four cleaning units 2031a, 2031b, 2031c, and 2031d (collectively called "cleaning units 2031"), four charging devices 2032a, 2032b, 2032c, and 2032d (collectively called "charging devices 2032"), four developing rollers 2033a, 2033b, 2033c, and 2033d (collectively called "developing rollers 2033"), a transfer belt 2040, a transfer roller 2042, a fixing device 2050, a paper feeding roller 2054, a paper ejection roller 2058, a paper feeding tray 2060, an ejection tray 2070, a communication controller 2080, an operation panel (not shown), and a printer controller 2090.

The communication controller 2080 controls bidirectional communication with an upper apparatus (for example, a personal computer) via a network or the like.

The printer controller 2090 includes a Central Processing Unit (CPU), a Read Only Memory (ROM) which stores programs written in codes interpretable for the CPU and various data sets used to execute the programs, a Random Access Memory (RAM) regarded as a memory for a work area, an amplification circuit, an analog to digital (A/D) conversion circuit which converts an analog signal into a digital signal. The printer controller 2090 controls each of parts in response to a request from the upper apparatus, and sends image information from the upper apparatus to the optical scanner 2010. Regarding multiple brands of recording papers as the recording media supportable for the color printer 2000, a developing condition and a transfer condition, which are suitable for each of a front side 2c and a back side 2d for each brand, are stored in the ROM as a "developing/transfer table".

The operation panel includes a display part which displays multiple keys and various information sets for an operator to perform various settings.

The photosensitive drum 2030a, the charging device 2032a, the developing roller 2033a, and the cleaning unit 2031a are used as a set, and form an image formation station (hereinafter, may be also called a "K station") which forms a black image.

The photosensitive drum 2030b, the charging device 2032b, the developing roller 2033b, and the cleaning unit 2031b are used as a set, and form an image formation station (hereinafter, may be also called a "C station") which forms a cyan image.

The photosensitive drum 2030c, the charging device 2032c, the developing roller 2033c, and the cleaning unit 2031c are used as a set, and form an image formation station (hereinafter, may be also called a "M station") which forms a magenta image.

The photosensitive drum 2030d, the charging device 2032d, the developing roller 2033d, and the cleaning unit 2031d are used as a set, and form an image formation station (hereinafter, may be also called a "Y station") which forms a yellow image.

A photosensitive layer is formed on a surface of each of the photosensitive drums 2030. Each of the photosensitive drums 2030 is rotated in an arrow direction within a corresponding surface in FIG. 1 by a rotating mechanism (not shown).

The charging devices 2032 uniformly charge surfaces of the respective photosensitive drums 2030.

The optical scanner 2010 respectively scans surfaces of the photosensitive drums 2030 being charged by light which is modulated for each color based on multi-color image information (the black image information, the cyan image information, the magenta image information, and the yellow image information) from the printer controller 2090. Thus, latent images corresponding to four sets of the image information are respectively formed on the surfaces of the photosensitive drums 2030. That is, each surface of the photosensitive drums 2030 corresponds to a scanning surface. Also, the photosensitive drums 2030 correspond to image carriers, respectively. The latent images are moved to a direction of corresponding developing rollers by rotation of the photosensitive drums 2030.

In accordance with rotations of the developing rollers 2033, toners from corresponding toner cartridges (not shown) are uniformly coated thinly on a surface of the developing rollers 2033. Thus, when contacting the surface of the photosensitive drums 2030, the toners on the surface of the developing rollers 2033 are transferred and adhered to portions alone on the surface of the photosensitive drums 2030, the portions on which corresponding lights are irradiated. That is, by the developing rollers 2033, the toners are adhered to a latent image formed on the surfaces of the corresponding photosensitive drums 2030 to form images. Then, the images (toner images) where the toners are adhered are moved toward the transfer belt 2040 in accordance with rotations of the corresponding photosensitive drums 2030.

The toner images of yellow, magenta, cyan, and black are sequentially transferred to the transfer belt 2040 at a predetermined timing, and are overlaid, so as to form a multi-color image.

The paper feeding tray 2060 stores recording papers. The paper feeding roller 2054 is arranged, and the paper feeding roller 2054 picks the recording paper out of the paper feeding tray 2060. The recording paper is conveyed into a gap between the transfer belt 2040 and the transfer roller 2042 at the predetermined timing. Accordingly, the toner images on the transfer belt 2040 are transferred onto the recording paper. The recording paper, on which the toner images are transferred, is conveyed to the fixing device 2050.

At the fixing device 2050, heat and pressure are applied to the recording paper. Hence, the toners are fixed on the recording paper. The recording paper, on which the tanners are fixed, is conveyed to the ejection tray 2070 via the paper ejection roller 2058, and is accumulated sequentially with other recording papers on the ejection tray 2070.

The cleaning units 2031 remove the toner (residual toners) left on the surfaces of the corresponding photosensitive drums 2030. After the residual toners are eliminated, the surfaces of the photosensitive drums 2030 are rotated again back at positions facing the corresponding charging devices 2032.

The sensor device 100 is arranged at a location near the operation panel in a state in which the operator can pick up, and is used to differentiate the brands of recording papers.

Figure 2:
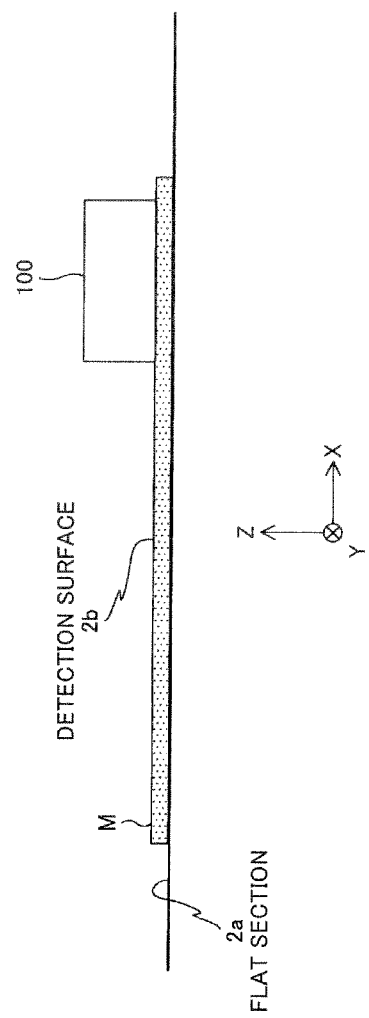
FIG. 2 is a diagram for explaining a position relationship between a sensor device and a recording paper.

When the brand of the recording paper is differentiated, the operator places a recording paper M on a flat section 2a provided near the operation panel, and puts the sensor device 100 on the recording paper M (see FIG. 2). In a xyz-3 dimensional orthogonal coordinate system, a direction orthogonal to a plane of the flat section 2a is defined as a z-axis direction. Then, the sensor device 100 is placed at a +Z side of the recording paper M. A surface of the +Z side of the recording paper M is called a "detection surface 2b".

Figure 3:
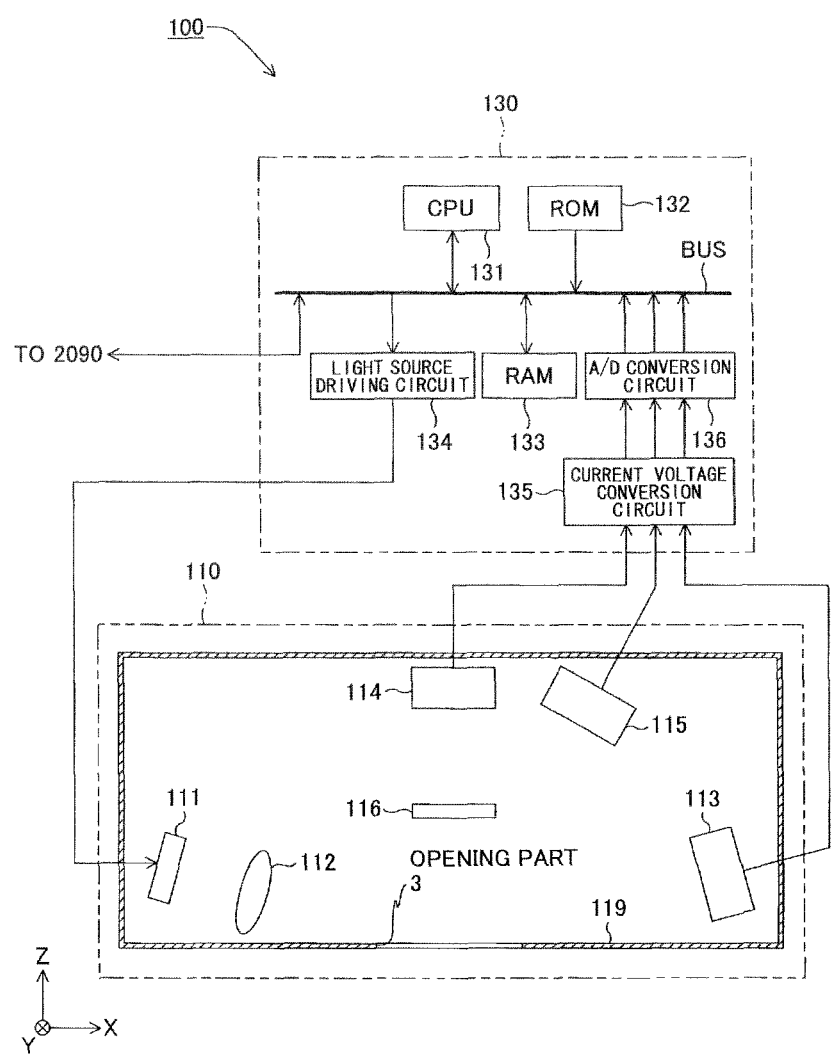
FIG. 3 is a diagram for explaining a configuration of the sensor device.

The sensor device 100 includes an optical sensor 110, and a processing apparatus 130, as depicted in FIG. 3 as an example.

The optical sensor device 110 includes a light source 111, a collimator lens 112, three optical receivers 113, 114, and 115, a polarizing filter 116, and a camera obscura 119 accommodating these components.

For example, the camera obscura 119 is a metal box material, for example, a box material made of aluminum. In order to reduce influence of disturbance light and stray light, a black alumite process is conducted on a surface of the camera obscure 119.

Figure 4:
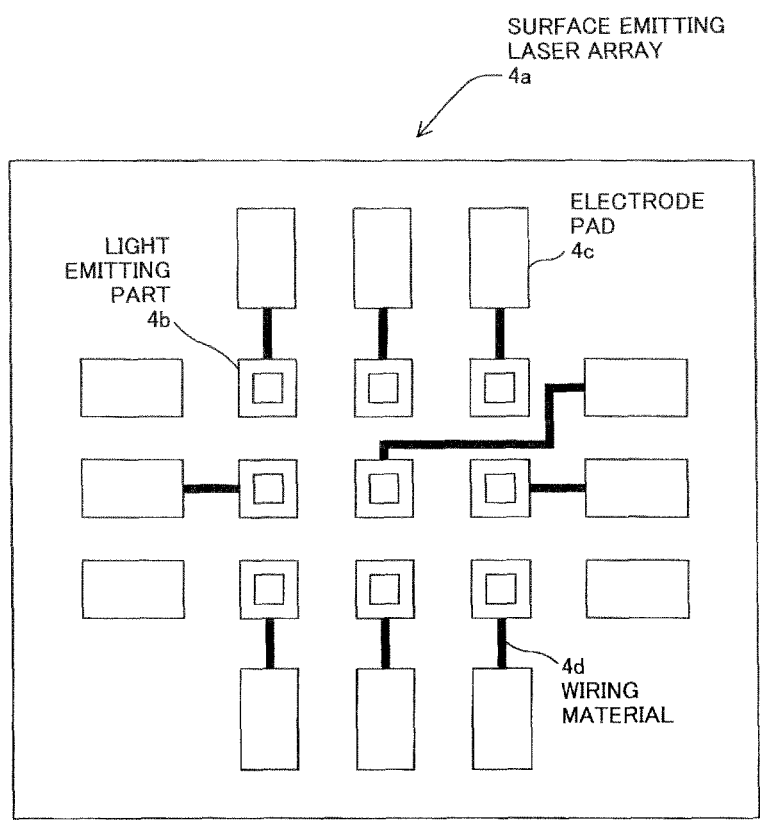
FIG. 4 is a diagram for explaining a surface emitting laser array.
Figure 5:
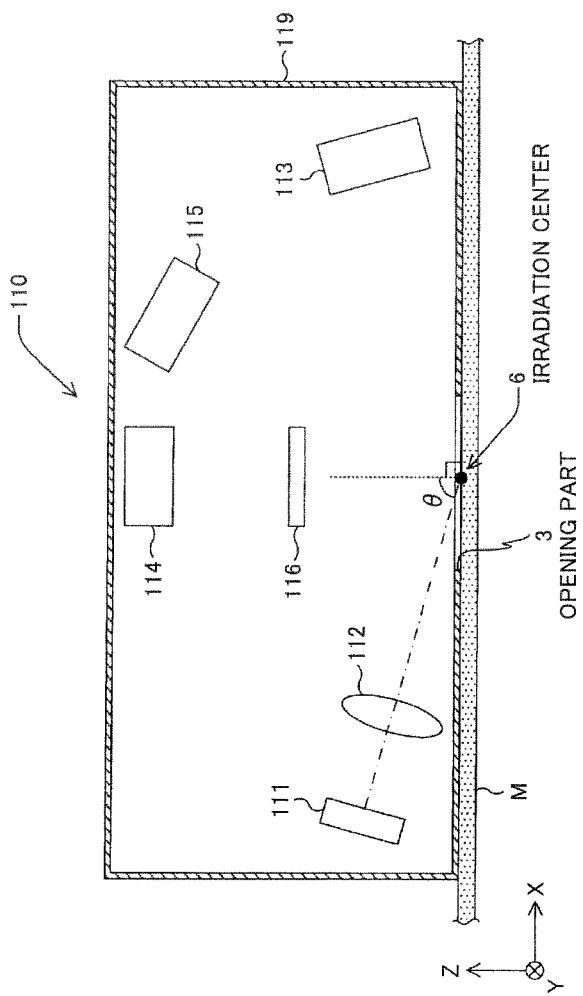
FIG. 5 is a diagram for explaining an incident angle θ of an irradiation light to a recording paper.

The light source 111 includes multiple light emitting parts 4b. Each of the light emitting parts is a Vertical Cavity Surface Emitting Laser (VCSEL). That is, the light source 111 includes a surface emitting laser array (VCSEL array) 4a. As depicted in FIG. 4 as an example, nine light emitting parts 4b are arranged by a two dimensional array. Each of the light emitting parts 4b is connected to an electrode pad 4c by a wiring material 4d.

The light source 111 is arranged so that a linear polarized light of a S-polarization is irradiated with respect to the recording paper M. Also, an entry angle θ (see FIG. 5) toward the recording paper M of the light from the light source 111 is 80°. The light source 111 is turned on and off by the processing apparatus 130.

The collimator lens 112 is arranged on a light path of the light emitted from the light source 111, and its light is regarded as an approximately parallel light. The light through the collimator lens 112 is irradiated to the recording paper M by passing an opening part 3 provided to the camera obscura 119. A center of an irradiation area on the detection surface 2b of the recording paper M is simply called an "irradiation center 6". Also, the light passing through the collimator lens 112 is also called "irradiation light 4".

When the light 4 enters an interface of a medium, a surface, which includes incident light and normal light of the interface drawn at an entry point, is called an "entry surface". In a case in which the incident light is formed by multiple beams, the entry surface exists for each of the multiple beams. For convenience of explanation, in the embodiment, the entry surface of the beam entering the irradiation center 6 is regarded as the entry surface with respect to the recording paper M. That is a surface, which includes the irradiation center 6 and is parallel to a xy-surface, is the entry surface with respect to the recording paper M.

In the embodiment, the S-polarization and a P-polarization are used not only for the incident light to the recording paper M but also for reflected light on the recording paper M, in which a polarization direction of the incident light to the recording paper M is defined as a reference in order to easily understand. Light in a same polarization direction as the incident light (here, the S-polarization) within an entry surface is called the S-polarization, and light in an orthogonal polarization direction to the incident light is called "P-polarization".

The polarizing filter 116 is arranged at the +Z side of the irradiation center 6. The polarization filter 116 is regarded as a polarization filter through which the P-polarization transmits and by which the S-polarization is blocked. Instead of using the polarization filter 116, a polarization beam splitter, which includes an equivalent function, may be used.

Figure 6:
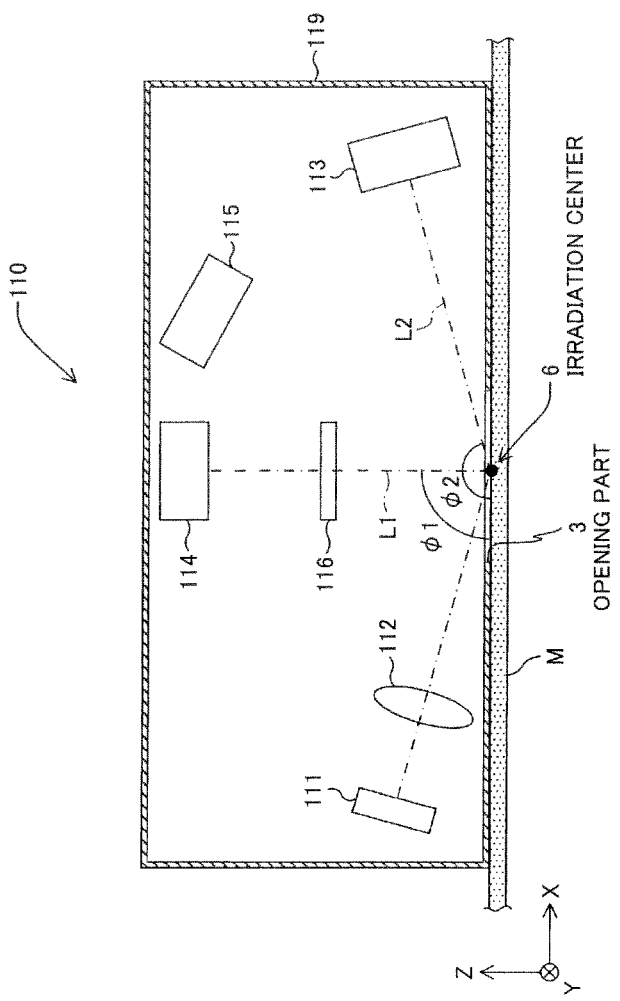
FIG. 6 is a diagram for explaining arrangement locations of a first optical receiver and a second optical receiver.

The optical receiver 114 is arranged at the +Z side of the polarization filter 116 and receives light passing through the polarization filter 116. As illustrated in FIG. 6, an angle ψ1, which is formed by a line L1 connecting the irradiation center 6, a center of the polarization filter 116, and a center of the optical receiver 114, and the detection surface 2b of the recording paper M.

The optical receiver 113 is arranged at a +X side of the irradiation center 6 regarding a X-axis direction, as depicted in FIG. 6, an angle ψ2, which is formed by a line L2 connecting the irradiation center 6 and a center of the optical receiver 113, and the detection surface 2b of the recording paper M, is 170°.

Figure 7:
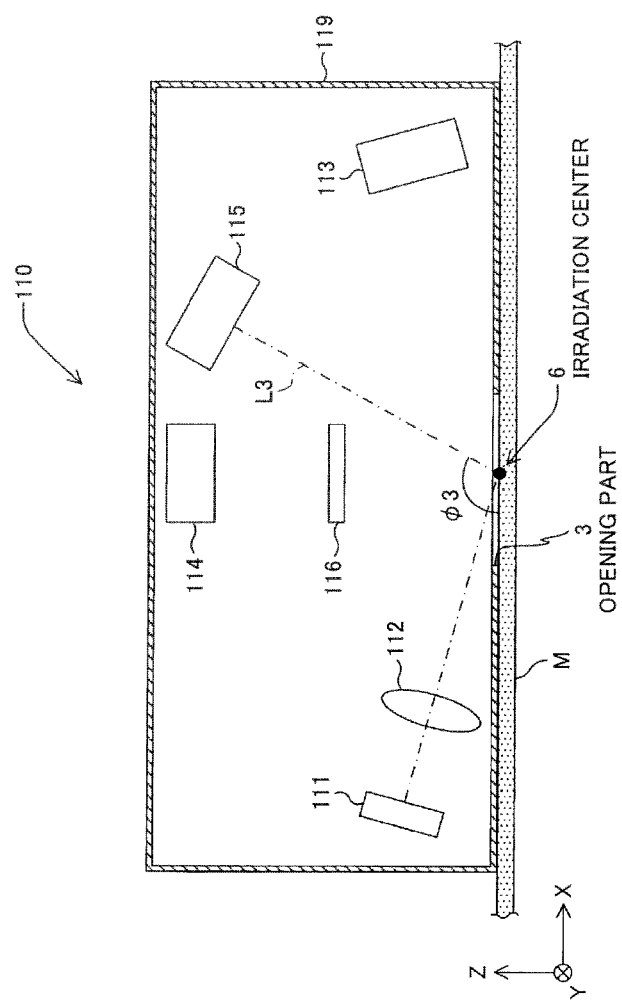
FIG. 7 is a diagram for explaining an arrangement location of a third optical receiver.

The optical receiver 115 is arranged at the +X side of the irradiation center 6 regarding the X-axis direction. As depicted in FIG. 7, an angle ψ3 is formed by a line L3 connecting the irradiation center 6 and a center of the optical receiver 115, and the detection surface 2b of the recording paper M. The angle ψ3 is 120°.

The center of the light source 111, the irradiation center 6, the center of the polarization filter 116, and the centers of the optical receivers 113, 114, and 115 exist approximately on the same plane.

Figure 8A:
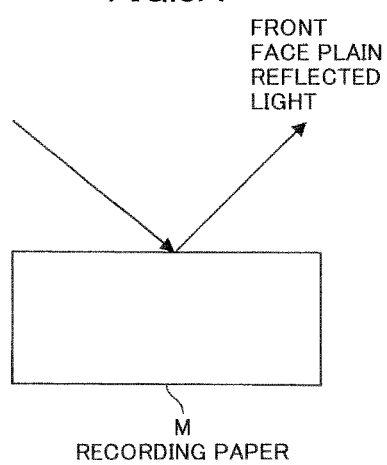
FIG. 8A is a diagram for explaining a surface regular reflected light.
Figure 8B:
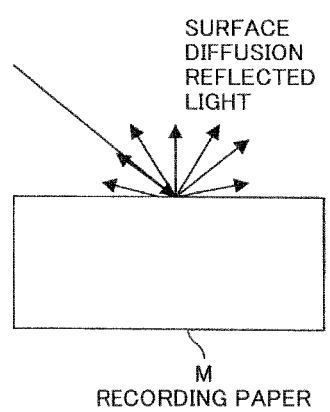
FIG. 8B is a diagram for explaining a surface diffusion reflected light.
Figure 8C:
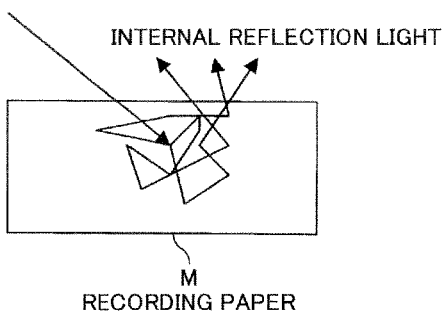

The reflected light from the recording paper M when the light is irradiated on the recording paper M may be considered by separating to reflected light which is reflected on the surface of the recording paper N and reflected light which is reflected light inside the recording paper M. Also, the reflected light being reflected on the surface of the recording paper M may be considered by further separating into reflected light through the specular reflection and reflected light through the diffusion reflection. In the following, for the sake of convenience, the reflected light through the specular reflection on the surface of the recording paper M is called a "front face regular reflected light", and the reflected light through the diffusion reflection on the surface of the recording paper M is called a "surface diffusion reflected light" (FIG. 8A and FIG. 8B).

The surface of the recording paper M is formed by planer portions and slope portions. Surface smoothness of the recording paper M is determined by its ratio. Light reflected at the planer portions becomes the front face regular reflected light, and light reflected at the slope portions becomes the surface diffusion reflected light. The surface diffusion reflected light corresponds to light reflected completely through the diffusion reflection, and it is regarded that a reflection direction of the surface diffusion reflected light is isotropic. The higher the smoothness is, the more a light quantity of the surface regular reflection light increases.

On the other hand, in a case of a plain printing paper, the reflected light from inside the recording paper M becomes the diffusion reflected light due to multiple scattering of light in fibers inside the recording paper M. In the following, for the sake of convenience, the reflected light from inside the recording paper M is also called an "internal reflected light" (see FIG. 8C). The reflected light from inside the recording paper M is also the light reflected completely through the diffusion reflection, similar to the surface diffusion reflected light, and its reflection direction is regarded to be isotropic.

The polarization directions of the surface regular reflected light and the surface diffusion reflected light toward the optical receivers 113, 114, and 115 are the same as the polarization directions of the incident light. In order for the polarization direction to rotate at the surface of the recording paper M, the incident light needs to be reflected at a surface inclining to a direction of the rotation with respect to an entry direction. The center of the light source 111, the irradiation center 6, and the centers of the optical receivers 113, 114, and 115 are on the same plane. Hence, the reflected light in which the polarization direction is rotated at the surface of the recording paper M is not reflected to any directions of the optical receivers 113, 114, and 115.

On the other hand, the polarization direction of internal reflected light coming to the optical receivers 113, 114, and 115 is rotated with respect to the polarization direction of the incident light, because it is considered that light entering inside the recording paper M passes fibers, and optically rotates so that the polarization direction is rotated.

Figure 9:
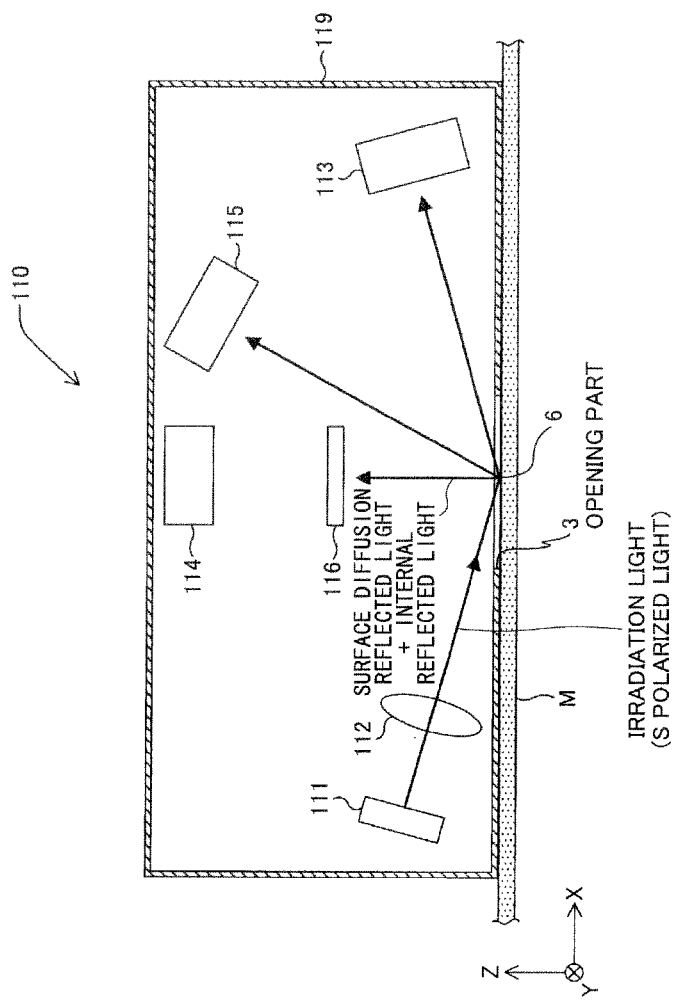
FIG. 9 is a diagram for explaining reflected light entering a polarization filter.
Figure 10:
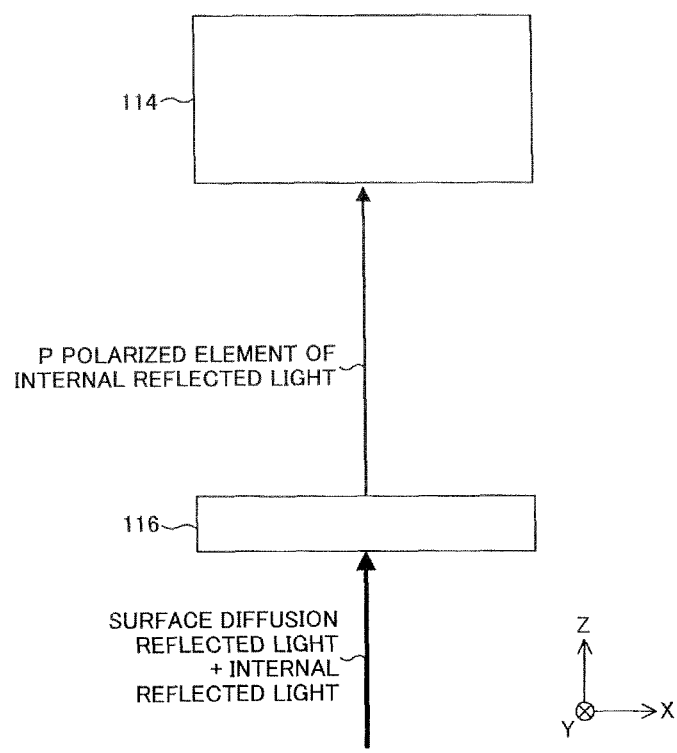
FIG. 10 is a diagram for explaining light received at the first optical receiver.
Figure 11:
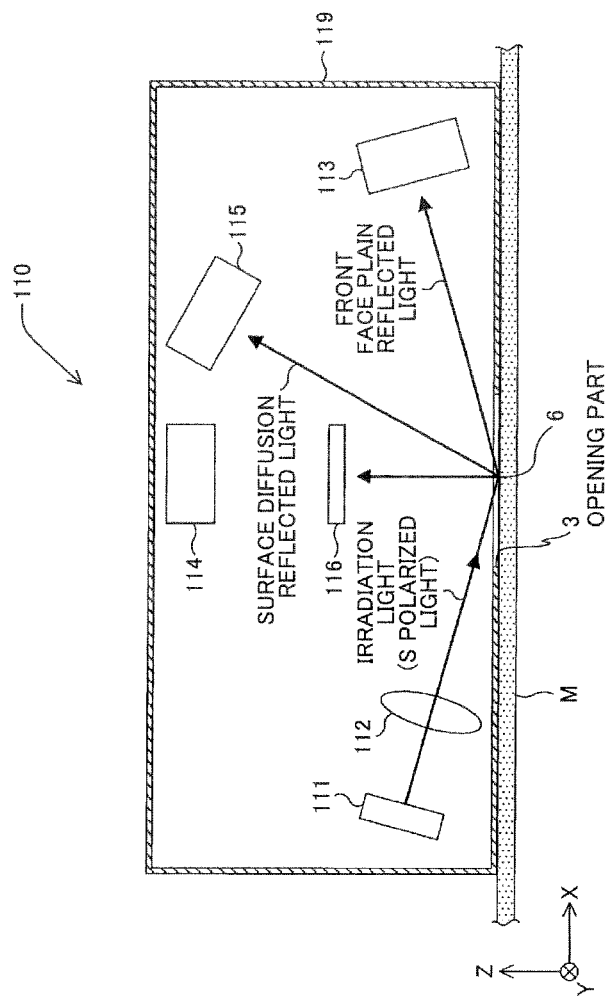
FIG. 11 is a diagram for explaining light received at the first optical receiver and the third optical receiver.
Figure 12A:
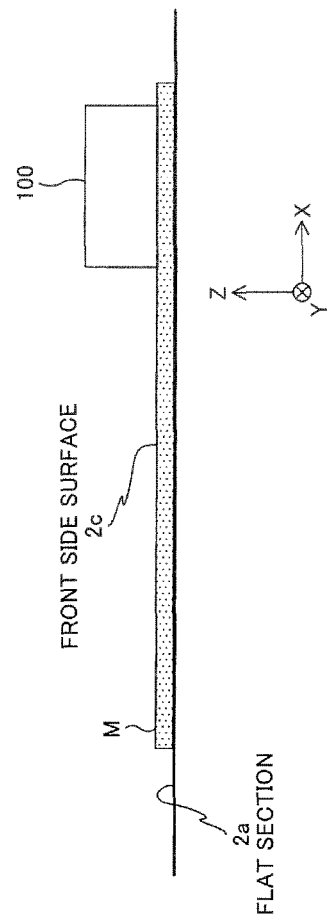
FIG. 12A is a diagram for explaining a case in which a surface of a front side of a recording paper is a detection surface.
Figure 12B:
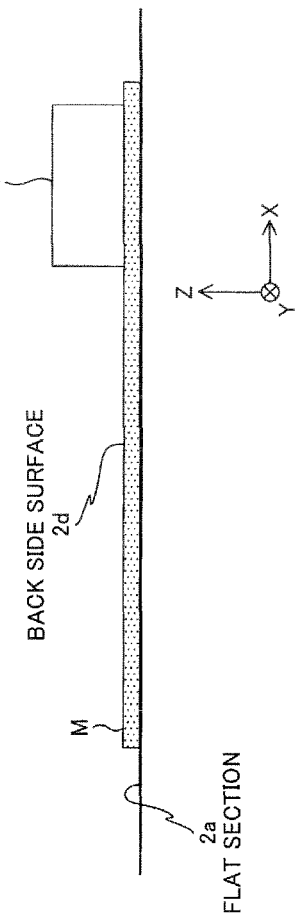
FIG. 12B is a diagram for explaining a case in which a surface of aback side of the recording paper is the detection surface.
Figure 14:
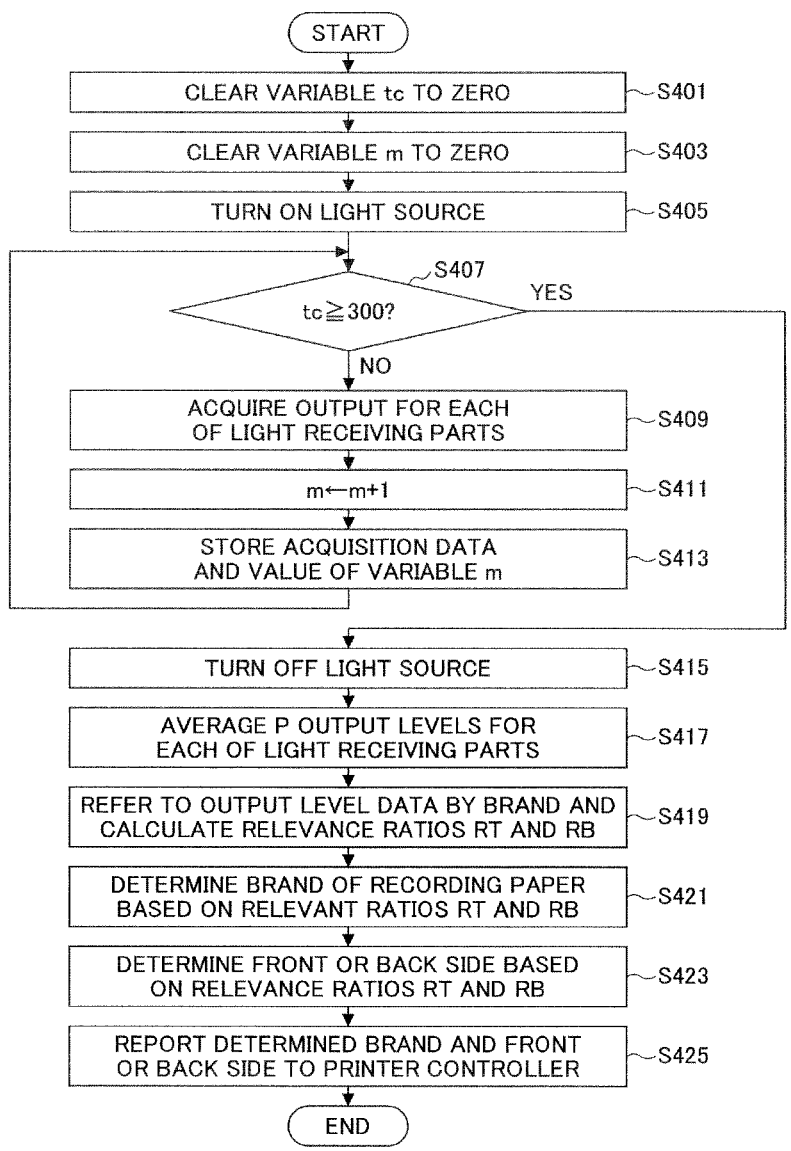
FIG. 14 is a flowchart for explaining a brand differentiation process.

The reflected light mixing the surface diffusion reflected light and the internal reflected light enters the polarization filter 116 (see FIG. 9).

The surface diffusion reflected light entering the polarization filter 116 has the same S-polarization as the incident light. Thus, the surface diffusion reflected light is blocked by the polarization filter 116. On the other hand, since the S-polarization and the P-polarization are mixed in the internal reflected light, the P-polarization component passes through the polarization filter 116. That is, the P-polarization component included in the internal reflected light is received by the optical receiver 114 (see FIG. 10). In the following, for the sake of convenience, the P-polarization component included in the internal reflected light is also called "P-polarization internal reflected light". Also, the S-polarization component included in the internal reflected light is also called "S-polarization internal reflected light".

The inventors confirmed that a light quantity of the P-polarization internal reflected light is correlated to thickness and density of the recording paper M, because it is considered that the light quantity of the P-polarization internal reflected light depends on a path length passing through fibers of the recording paper M.

The reflected light mixing the surface regular reflected light, the surface diffusion reflected light, and the internal reflected light enters the optical receiver 113. At this light reception position, the light quantities of the surface diffusion reflected light and the internal reflected light are significantly smaller than the light quantity of the surface regular reflected light. Hence, a light reception quantity of the optical receiver 113 is regarded as the light quantity of the surface regular reflected light (see FIG. 11).

The reflected light mixing the surface diffusion reflected light and the internal reflected light enters the optical receiver 115. At this light reception position, the light quantity of the internal reflected light is significantly smaller than the light quantity of the surface diffusion reflected light. Hence, the light reception quantity of the optical receiver 115 is regarded as the light quantity of the surface diffusion reflected light (see FIG. 11).

Each of the optical receivers 113, 114, and 115 outputs an electronic signal respective to a corresponding light reception quantity to the processing apparatus 130.

Returning to FIG. 3, the processing apparatus 130 includes a CPU 131, a ROM 132, a RAM 133, a light source driving circuit 134, a current voltage conversion circuit 135, and an A/D conversion circuit 136.

The ROM 132 stores programs written in codes interpretable for the CPU 131 and various data sets used to execute the programs. RAM 133 is used for a working area.

The light source driving circuit 139 outputs a light source driving signal to the light source 111 in response to an instruction of the CPU 131.

The current voltage conversion circuit 135 converts current signals from the optical receivers 113, 114, and 115 into voltage signals. The A/D conversion circuit 136 converts the voltage signals from analog signals to digital signals, from the current voltage conversion circuit 135.

The CPU 131 determines the brand of the recording paper M in accordance with a program stored in the ROM 132. A determination result is reported to the printer controller 2090.

The processing apparatus 130 is fixed to the camera obscure 119. The optical sensor 110 and the processing apparatus 130 may be accommodated in a chassis having an outer shape so that the operator can easily pick it up with his/her hand.

In the embodiment, regarding the recording papers M having different brands supportable for the color printer 2000, the color printer 2000 acquires, beforehand, an output level from each of the optical receivers 113, 114, and 115 in a case in which a surface of a front side of the recording paper M is placed as the detection surface 2c (see FIG. 12A) and the light source 111 of the optical sensor 110 is lighted. Also, the color printer 2000 acquires, beforehand, an output level from each of the optical receivers 113, 114, and 115 in a case in which a surface of a back side of the recording paper M is placed as the detection surface 2b (see FIG. 12B) and the light source 111 of the optical sensor 110 is lighted.

Acquisition results are stored as output level data T13 by brand in the ROM 132 of the processing apparatus 130. That is, the output level data T13 by brand correspond to a database including output data of multiple optical receivers 113, 114, and 115 which are acquired beforehand in both cases of placing the surfaces of the front side and the back side of the recording paper M as the detection surface 2b, regarding the recording papers M being brands different from each other in which each of the brands is known.

In the output level data T13 by brand, in a case in which the surface of the front side of the recording paper M is placed as the detection surface 2b, S1T represents the output level of the optical receiver 113, S2T represents the output level of the optical receiver 114, and S3T represents the output level of the optical receiver 115. Ina case in which the surface of the back side of the recording paper M is placed as the detection surface 2b, S1B represents the output level of the optical receiver 113, S2B represents the output level of the optical receiver 114, and S3B represents the output level of the optical receiver 115 (see FIG. 13). That is, S1T, S2T, and S3T correspond to first output data 13-1, and S1B, S2B, and 53B correspond to second output data 13-2.

Next, a process (a brand differentiation process) for determining the brand of the recording paper M which brand is unknown will be described.

First, operations conducted by the operator will be described for the brand differentiation process.
1. Place the recording paper M of a differentiation target on the flat section 2a.
2. Pick up the sensor device 100 by hand, and put the sensor device 100 on the recording paper M.
3. Input a differentiation process request through the operation panel.

The differentiation process request is reported to the processing apparatus 130 of the sensor device 100 through the printer controller 2090 from the operation panel.

The processing apparatus 130 starts the brand differentiation process when receiving the differentiation process request. A flowchart in FIG. 14 corresponds to a series of process algorithms executed by the CPU 131 of the processing apparatus 130 for the brand differentiation process.

In first step S401, a variable to is cleared to zero. The variable tc is used to store a value of a timer counter. As one example, a value of the variable tc is incremented by +1 in a timer interruption process caused every 10 ms.

In next step S403, a variable m is cleared to zero. The variable m is used to store a count of acquiring the output signal from each of the optical receivers 113, 114, and 115.

In next step S405, the light source 111 is turned on. In this case, the multiple light emitting parts 4b are simultaneously turned on.

In next step S407, it is determined whether the value of the variable tc is greater and or equal to 300. That is, it is determined whether time lapses 3 seconds after the light source 111 is turned on. If a determination indicates negative, the process advances to step S409.

In step S409, the output signal for each of the optical receivers 113, 114, and 115 is acquired.

In step S411, the value of a variable m is incremented by 1.

In step S413, data acquired in step S409 are stored with the value of the variable m in the RAM 133. Then, the process goes back to step S407.

In the following, steps S409 through S413 are repeated until the determination in step S407 indicates positive.

When the determination in step S407 indicates positive, the process advances to step S415.

In step S415, the light source ill is turned off. If the value of the variable m indicates P at time of step S415, P sets of data are stored for each of the optical receivers 113, 114, and 115 in the RAM 133.

In next step S417, P output levels are averaged for each of the optical receivers 113, 114, and 115. S1' indicates an average value of the output level of the optical receiver 113, S2' indicates an average value of the output level of the optical receiver 114, and S3' indicates an average value of the output level of the optical receiver 115. S1', S2', and S3' are measurement data.

In next step S419, the output data T31 by brand stored in the ROM 132 are referred to, a relevance ratio RT is calculated by using the following formula (1), and a relevance ratio RB is calculated by using the following formula (2).

$$RT = \left(1 - \left|\frac{S1T - S1'}{S1T + S1'}\right|\right) \times \left(1 - \left|\frac{S2T - S2'}{S2T + S2'}\right|\right) \times \left(1 - \left|\frac{S3T - S3'}{S3T + S3'}\right|\right) \quad (1)$$

$$RB = \left(1 - \left|\frac{S1B - S1'}{S1B + S1'}\right|\right) \times \left(1 - \left|\frac{S2B - S2'}{S2B + S2'}\right|\right) \times \left(1 - \left|\frac{S3B - S3'}{S3B + S3'}\right|\right) \quad (2)$$

In next step S421, the brand having the greatest relevance ratio RT or RB is selected, and the selected brand is determined as the brand of the recording paper M.

In next step S423, based on relevance ratios RT and RB, it is determined whether the detection surface 2b is the surface of the front side or the surface of the back side. If RT>RB, it is determined that the detection surface 2b is the surface of the front side. If RT<RB, it is determined that the detection surface 2b is the surface of the back side.

In next step S425, the brand, and the front or back side of the recording paper M, which are determined, are reported to the printer controller 2090. Then, the brand differentiation process is terminated.

Figure 15A:
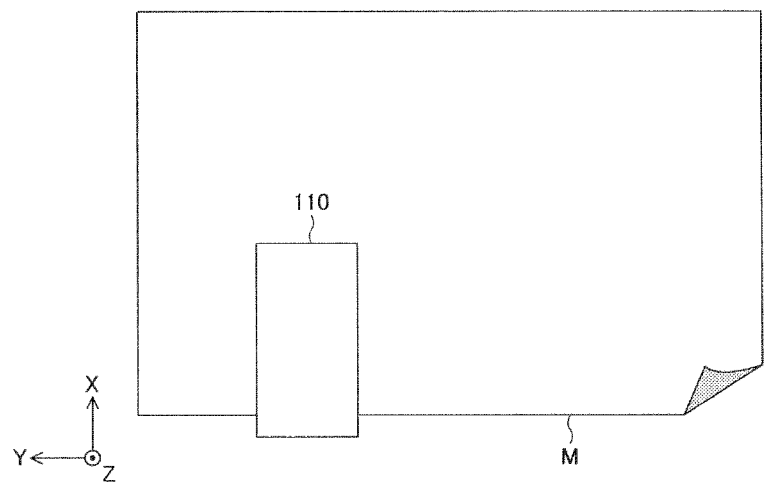
FIG. 15A and FIG. 15B are diagrams for explaining a relative movement of the sensor device with respect to the recording paper.
Figure 15B:
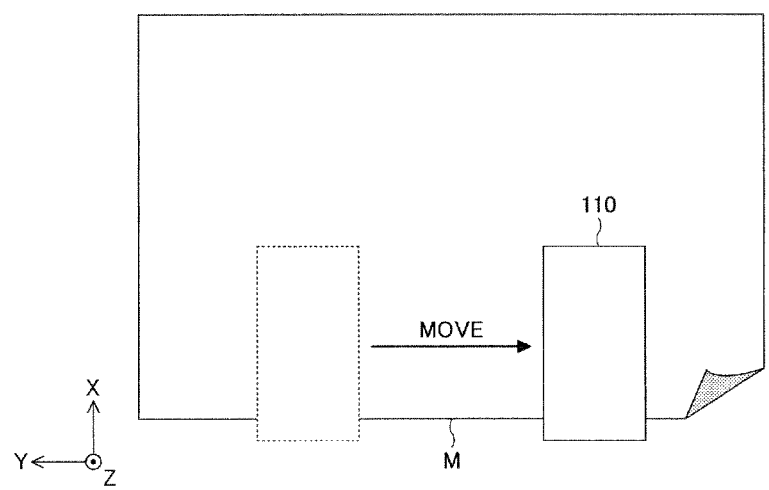
Figure 16:
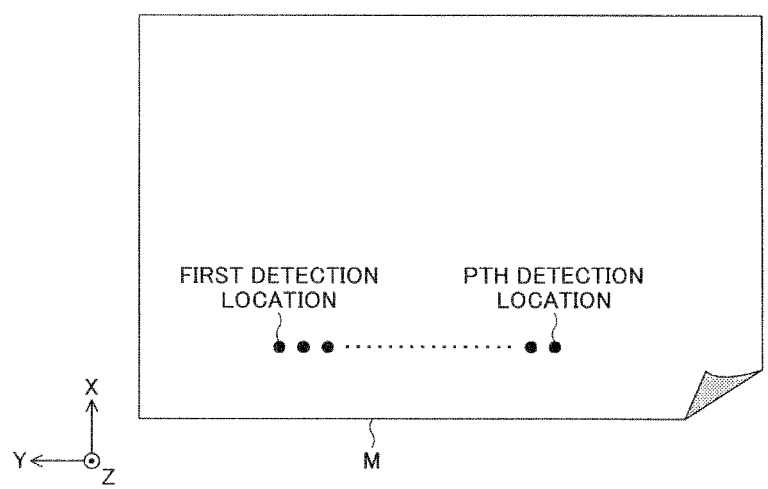
FIG. 16 is a diagram for explaining a detection location when the sensor device is relatively moved with respect to the recording paper.

As depicted in FIG. 15A and FIG. 15B as an example, while the light source 111 is being turned on in the brand differentiation process, the operator may move either one of the sensor device 100 and the recording paper M. In this case, as depicted in FIG. 16 as an example, P different locations may be defined as detection locations for the recording paper M. It should be noted that the P different locations may not be always at even intervals.

Also, while the light source 111 is turned on in the brand differentiation process, in a case in which the operator does not move any of the sensor device 100 and the recording paper M, data are acquired P times at one detection location.

The printer controller 2090 displays the brand and the front or back side of the recording paper M, which are determined by the sensor device 100, at a display part of the operation panel, and stores data in the RAM.

When the brand and the front or back side of the recording paper M, which are determined by the sensor device 100, are displayed at a display part of the operation panel, the operator returns the sensor device 100 to an original arrangement location. Then, the operator sets the recording paper for which the brand and the front or back side are determined, at the paper feeding tray 2060. The operator may register the brand and the front or back side, which are displayed at the display part of the operation panel, in the printer controller 2090 by using keys of the operation panel.

When receiving a print job request, the printer controller 2090 reads out information of the brand and the front or back side of the recording paper M stored in the RAM. The printer controller 2090 acquires a phenomena condition and a transfer condition suitable for the brand and the front or back side of the recording paper M, from the developing/transfer table.

Then, the printer controller 2090 controls a developing device and a transfer device for each of the K station, the C station, the M station, and the Y station. For example, a transfer voltage and a toner amount are controlled. Then, a high quality image is formed on the recording paper M.

Even if the recording paper M is a plain paper on which a surface process is not conducted, a property of smoothness and the like becomes different for each surface of the front side and the back side depending on a production process. That is, due to a production method, the recording paper M has differences in a surface state, an internal configuration in vicinity of the surface, and the like between the surfaces of the front side and the back side. Accordingly, even for the same recording paper M, a different reflection property may be acquired depending on the surface where the light is illuminated (see FIG. 17A and FIG. 17B).

Figure 17A:
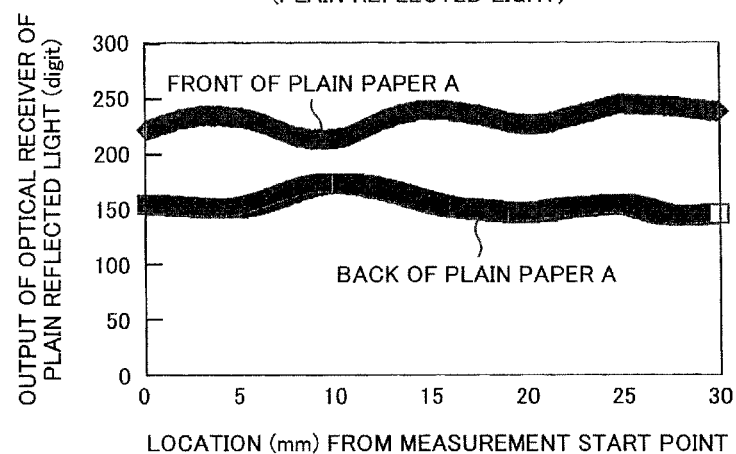
FIG. 17A and FIG. 17B are diagrams for explaining a difference of an optical property between a front side and a backside of the regular paper for each of the recording papers.
Figure 17B:
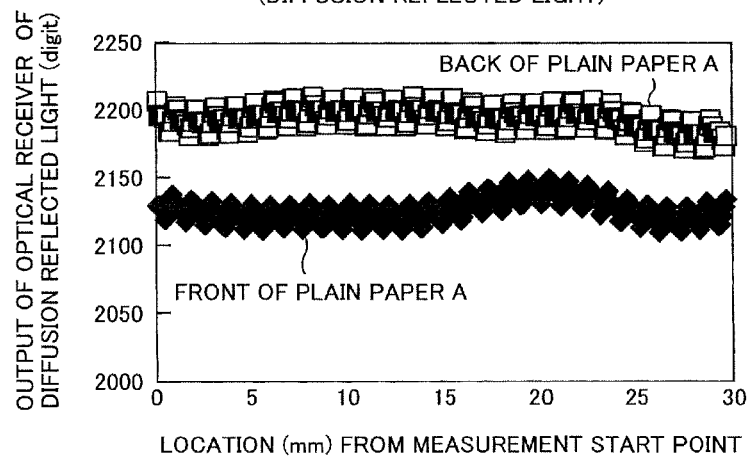

In FIG. 17A and FIG. 17B, with respect to a front surface and a back surface of the plain paper on which one-side coating process is not conducted, light reception quantities of the regular reflected light and the diffusion reflected light are acquired at multiple locations on each of the front and back surfaces by using the optical sensor 110, and acquisition results are illustrated. The light acquisition quantity of the regular reflected light is greater on the front surface than the back surface. Regarding this brand, the smoothness of the front surface indicates high, and thus, a ratio of the light quantity, in which light is diffused inside the recording paper M, becomes lower. Accordingly, a reflectance becomes great.

Especially, in recent production printers requiring high quality, a print condition setting is demanded to correspond to a slight difference between the surfaces of the front side and the back side. Accordingly, the print condition suitable for the surface to be printed is set for the image formation at higher quality. In a case of filling up a tray with the recording papers M, it is needed to set a printing surface to be an appropriate direction. The operator is required to differentiate the front and back sides of the recording paper M. Thus, a setting operation is complicated.

Moreover, in an image forming apparatus in which the print condition is optimized with respect to the front surface of the recording paper M for each of the brands, if the front or back of the recording paper M is erroneously set, it is difficult to acquire a high quality image. Furthermore, the erroneous setting may cause a failure of the image forming apparatus.

In order to detect properties such as a type and the surface state of the recording paper M, an optical method has been widely used in which light is irradiated from a light emitting element, and its reflected light and transmission light are received by a light receiving element.

The Patent Document 1 discloses a recording material differentiation apparatus for determining the type of the recording material by using the reflected light and the transmission light, in which a front surface of a recording paper is read out by an imaging element such a Charge Coupled Device (CCD) or the like, and the recording paper is differentiated based on a pattern captured by the imaging element.

However, in the technology of Patent Document 1, blurring occurs to a read image, and a high quality image is not acquired. Thus, the recording papers are not properly differentiated. In order to reduce occurrences of blurring, an imaging element having higher performance is required, but costs more. Moreover, even if the high quality image is acquired, an image analysis apparatus with high performance is needed to differentiate the recording papers.

Accordingly, a recording paper differentiation sensor is required to have a simpler configuration and to be a non-contact type. A reflected light system is a system which satisfies this condition. The reflected light system emits the light on the recording paper from the light source 111, and differentiates the recording papers by a reflected light quantity. Conventional technologies of the reflected light system are classified into three types represented by the following three Patent Documents.

Accordingly, as disclosed in Patent Document 2, one technology emits light on a surface of a measurement object and measures the reflected light quantity in the regular reflection direction. This technology is known as a specular gloss measurement method (JIS-Z8741). In the specular gloss measurement method, parallel light is emitted on the measurement object with a specified incident angle, a reflected light quantity in the regular reflection direction is detected by a light detector, and a value, which is normalized by the reflection light quantity detected on a standard surface (a glass of a refractive index 1.567), is defined as specular glossiness.

In the specular gloss measurement method, it is generally preferable to use a measurement method having a smaller incident angle to measure a measurement object having a greater specular glossiness, and to use another measurement method having a greater incident angle to measure a measurement object having lesser specular glossiness.

In a second method, as disclosed in Patent Document 3, scattered and reflected light quantities are measured. The second method is based on the specular gloss measurement. Multiple light receiving parts are provided, and a type of the measurement object is differentiated based on a reflected light quantity in a regular reflection direction and a reflected light quantity in another reflection direction. The multiple light receiving parts are arranged in a direction different from the regular reflection direction. When the light is illuminated on a paper sheet having irregularity in a relatively flat surface state such as the plain paper, a light quantity, which is scattered to a direction different from the regular reflection direction due to the irregularity, is detected and the type of the recording paper is discriminated. That is, the smoothness of the recording paper is detected and the recording paper is discriminated based on a ratio of the scattered and reflected light quantity to the regular reflected light quantity.

A third method, as disclosed in Patent Document 4, measures the regular reflected light by separating a light beam by a polarization beam splitter. In Patent Document 4, a light source section is provided to change light emitted from a light emission diode (LED) to a linear polarization with respect to a polarization filter. The reflected light in the regular reflection direction is separated into a S-wave and a P-wave by the polarization beam splitter. A surface state of the recording paper is differentiated based on these detected values. Based on a table acquired beforehand in which types are classified into three types, namely a non-coated paper, a coated paper, and an overhead projector (OHP) sheet, the type of the recording paper is differentiated.

In the above described technologies for differentiating a paper type by a simple configuration, only a difference among the plain paper, the coated paper, and the OHP sheet is detected. It is difficult to specify the brand necessary for the high quality image formation.

Also, Patent Document 5 discloses an optical sensor which emits light of the linear polarization on a surface at one side of the recording paper, detects the regular reflected light and the polarization component orthogonal to the polarization of the irradiation light included in the diffusion reflected light, and determines the brand of the recording paper. According to Patent Document 5, it is possible to determine not only types of the paper sheets such as the non-coated paper, the coated paper, and the OHP sheet but also a detailed brand of the paper sheet. However, in a case of determining the brand of the paper sheet having different properties for the front surface and the back surface, this technology may estimate a different brand when the front surface is measured and when the back surface is measured.

Also, there are the following conventional technologies related to a technology for determining the type of the paper sheet having a different property between the front surface and the back surface.

Patent Document 6 discloses to emit light on a surface to record and a back surface of the recording paper, to measure reflectance of the light on each of the surfaces, and to combine a difference value between the reflectance of the surfaces with an absolute value which is measured beforehand, so as to determine the type of the recording paper.

Patent Document 7 discloses to emit the light on the recording surface and the back surface of the recording paper, and to detect the regular reflected light and the diffusion reflected light for each of the surfaces, so as to differentiate the front side and the backside of the recording paper.

According to the embodiment, for the recording paper M having a different type for each of the surfaces of the front side and the back side in which for example, the surface of the front side is formed as the coated paper and the surface of the back side is formed as the plain paper, it is possible to differentiate the front and back sides and the type of the recording paper M (the coated paper, the non-coated paper, and the OHP sheet). However, after determining the brand necessary for the high quality image formation, it may be difficult to identify a difference between the surface of the front side and the surface of the back side of the recording paper M such as the plain paper to which the one-side coating process is not conducted.

The sensor device 100 of the embodiment measures the output level from each of the optical receivers 113, 114, and 115 for the recording paper M of the differentiation target, and calculates the relevance ratios RT and/or RB of the measured output level to the output level for each of the optical receivers 113, 114, and 115 included in the output level data T13 by brand, so as to differentiate the brand and the front or back side of the recording paper M of the determination target. The output level data T13 by brand is referred by the sensor device 100 when the sensor device 100 determines the brand of the recording paper, and indicates the output level for each of the optical receivers 113, 114, and 115 in a case of emitting the light on the surface of the front side of the recording paper M and in a case of emitting the light on the surface of the back side of the recording paper M.

As described above, the sensor device 100 according to the embodiment includes the optical sensor 110, a processing apparatus 130, and the like.

The processing apparatus 130 includes the CPU 131, the ROM 132, the RAM 13, the light source 111 driving circuit 134, the current voltage conversion circuit 135, the A/D conversion circuit 136, and the like. For each of the recording papers of multiple brands supportable for the color printer 2000, the ROM 132 stores information of the output level for each of the optical receivers 113, 114, and 115 when the light source 111 of the optical sensor 110 is turned on in a case of setting the surface of the front side of the recording paper M as the detection surface 2b, and also stores information of the output level for each of the optical receivers 113, 114, and 115 when the light source ill of the optical sensor 110 is turned on in a case of setting the surface of the back side of the recording paper M as the detection surface 2b.

After that, for the recording paper M of the determination target, the CPU 131 measures the output level of each of the optical receivers 113, 114, and 115 when the light source 111 of the optical sensor 110 is turned on, calculates the relevance ratio RT from the above formula (1) by referring to the output level data T13 by brand, and calculates the relevance ratio RB from the above formula (2). Moreover, the CPU 131 determines the brand and the front or back side of the recording paper M of the determination target based on the relevance ratio PT and the relevance ratio RB.

Accordingly, it is possible for the sensor device 100 to differentiate an object by the simple configuration at high accuracy.

Also, in the embodiment, since the surface emitting laser array 4a is used as the light source 111, there is no need for the polarization filter for acquiring the irradiation light 4 of the linear polarization. Furthermore, by using the emitting laser array 4a, it is possible to integrate the multiple light emitting parts 4b at higher density, which is difficult for the LED and the like which are conventionally used.

In the embodiment, it is possible to realize the light source 111 which includes the multiple light emitting parts 4b and is a small type. Also, since all laser beams are collected in a vicinity of a light axis of the collimator lens 112, it is possible to make the incident angle constant so as to make multiple lights parallel. In this case, a cheaper collimator optical system may be used. Hence, it is possible to reduce a size of the optical sensor and to lower costs.

Also, in the brand differentiation process, the multiple light emitting parts 4b of the emitting laser array 4a are simultaneously turned on. Accordingly, it is possible to improve a signal-noise ratio (S/N) of an output from each of the optical receivers 113, 114, and 115 and to improve differentiation accuracy.

Also, a contrast ratio of a speckle pattern is reduced by simultaneously turning on the multiple light emitting parts 4b, and a further accurate reflected light amount is acquired. Thus, it is possible to improve the differentiation accuracy.

Also, it is possible to increase an amount of the internal reflected light by simultaneously turning on the multiple light emitting parts 4b. In the optical sensor 110, it is possible to separate the reflected light from inside the recording paper M at high accuracy, the reflected light being conventionally difficult to be separated due to its weakness. The reflected light from inside the recording paper M includes information pertinent to an internal state of the recording paper M.

Then, the CPU 131 determines the brand of the recording paper M from output signals from the three optical receivers 113, 114, and 115. That is, by considering the information pertinent to the internal state of the recording paper M, a differentiation level of the recording paper M is improved until it can be used for a brand level which has been conventionally difficult.

Also, instead of combining multiple types of sensors, a simple component configuration is realized. Accordingly, it is possible to realize a sensor small in size.

The color printer 2000 according to the embodiment is provided with the sensor device 100. As a result, without causing high cost and an increase in size, it is possible to form the high quality image. Moreover, it is possible to resolve trouble in conventional manual setting and a printing failure due to setting mistakes.

In the embodiment, if it is easy to differentiate the surface of the front side and the surface of the back side in the recording paper M, a first output level and a second output level may be respectively measured in the brand differentiation process, the first output level for each of the optical receivers 113, 114, and 115 being a case in which the surface of the front side is set as the detection surface 2b, the second output level for each of the optical receivers 113, 114, and 115 being a case in which the surface of the back side is set as the detection surface 2b. In this case, the processing apparatus 130 may calculate the relevance ratio RT by using the following formula (3), calculate the relevance ratio RB by using the following formula (4), and determine a brand having a maximum value of RT×RB as the brand of the recording paper M. This case will be described below as a first variation of the embodiment.

$$RT = \left(1 - \left|\frac{S1T - S1T'}{S1T + S1T'}\right|\right) \times \left(1 - \left|\frac{S2T - S2T'}{S2T + S2T'}\right|\right) \times \left(1 - \left|\frac{S3T - S3T'}{S3T + S3T'}\right|\right) \quad (3)$$

In the formula (3), S1T' indicates an average value of the output level of the light receiver 113, S2T' indicates an average value of the output level of the light receiver 114, and S3T' indicates an average value of the output level of the light receiver 115, when the surface of the front side is set as the detection surface 2b. S1T', S2T', and S3T' correspond to first measurement data.

$$RB = \left(1 - \left|\frac{S1B - S1B'}{S1B + S1B'}\right|\right) \times \left(1 - \left|\frac{S2B - S2B'}{S2B + S2B'}\right|\right) \times \left(1 - \left|\frac{S3B - S3B'}{S3B + S3B'}\right|\right) \quad (4)$$

In the formula (4), S1B' indicates an average value of the output level of the light receiver 113, S2B' indicates an average value of the output level of the light receiver 114, S3B' indicates an average value of the output level of the light receiver 115, when the surface of the back side is set as the detection surface 2b. S1B, S2B', and S3B' correspond to second measurement data.

In the first variation, operations conducted by the operator will be described.

1. Place the recording paper M of the differentiation target on the flat section 2a so that the surface of the front side is set as the detection surface 2b.
2. Pick up the sensor device 100 by hand, and place the sensor device 100 on the recording paper M.
3. Input the differentiation process request via the operation panel.

Figure 18:
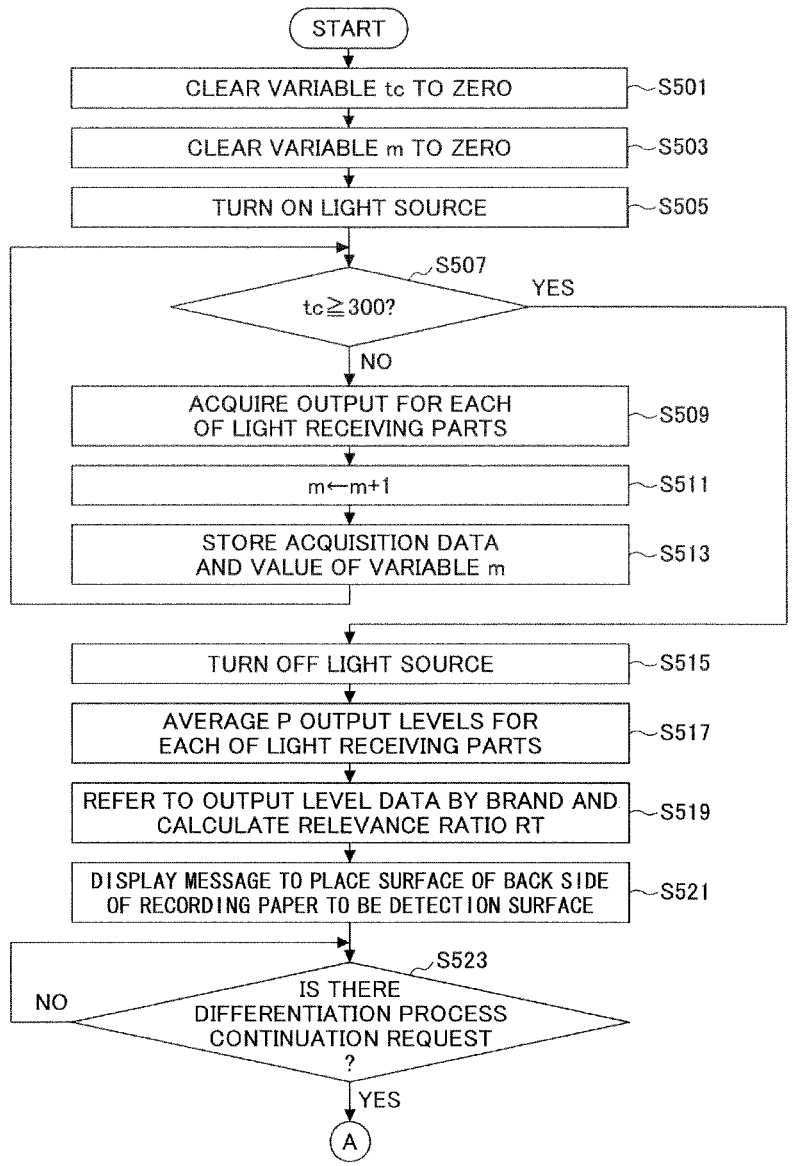
FIG. 18 is a flowchart for explaining a first variation of a brand differentiation process (part 1)
Figure 19:
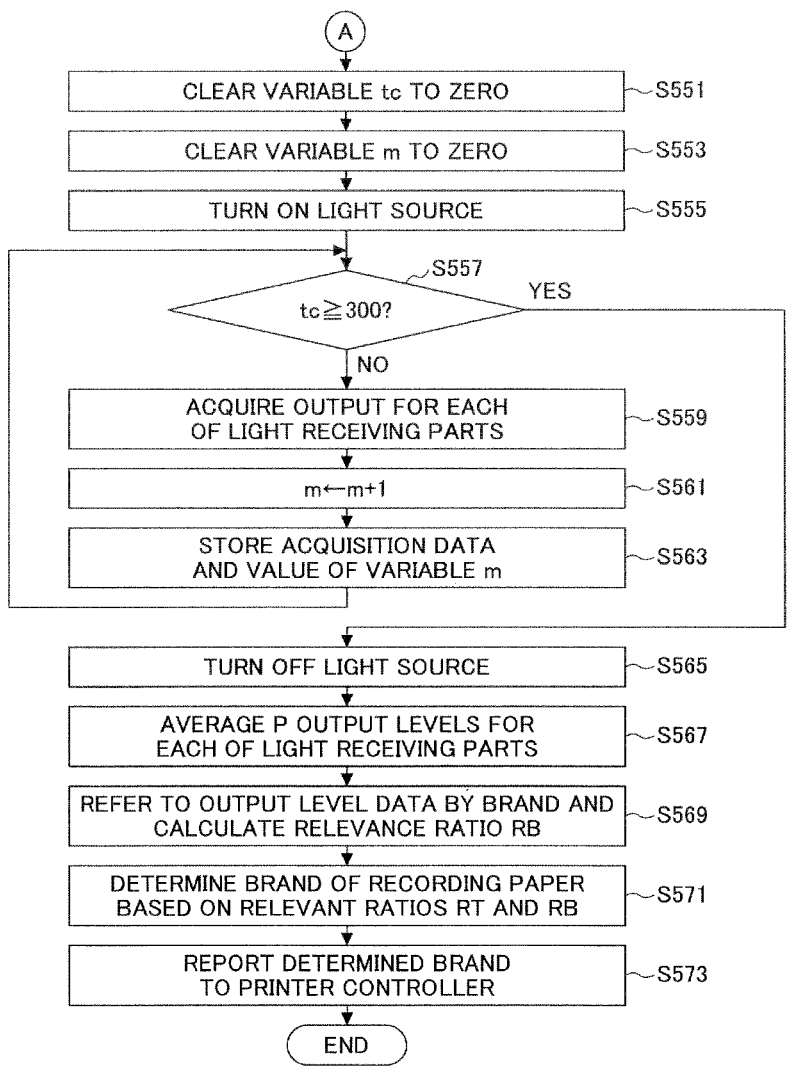
FIG. 19 is a flowchart for explaining the first variation of the brand differentiation process (part 2)

A flowchart for the first variation of the embodiment illustrated in FIG. 18 and FIG. 19 corresponds to a series of process algorithms executed by the CPU 131 of the processing apparatus 130 for the brand differentiation process.

First steps S501 through S517 are the same as steps S401 through S417 described above.

In next step S519, the output level data T13 by brand stored in the ROM 132 are referred to, and the relevance ratio RT is calculated by using the above formula (3) for each of brands.

In next step S521, a message is displayed at the display part of the operation panel via the printer controller 2090 to instruct the operator to place the surface of the back side of the recording paper M to be the detection surface 2b.

The operator places the surface of the back side of the recording paper M to be the detection surface 2b in accordance with the message, and inputs a differentiation process continuation request via the operation panel. The differentiation process continuation request is reported to the processing apparatus 130 of the sensor device 100 via the printer controller 2090 from the operation panel.

When the processing apparatus 130 receives the differentiation process continuation request, a determination in step S523 indicates positive, and the process advances to step S551.

Steps S551 through S567 are the same as steps S401 through S417 described above.

In next step S569, the output level data T13 by brand stored in the ROM 132 is referred to, and the relevance ratio RB is calculated by using the above formula (4) for each of the brands.

In next step S571, the brand having the maximum value of RT×RB is selected, and the selected brand is determined as the brand of the recording paper M.

In next step S573, the brand of the recording paper M is reported to the printer controller 2090. After that, the brand differentiation process is terminated.

Also, in the embodiment, if it is difficult to differentiate the surface of the front side and the surface of the back side for the recording paper M, a first output level and a second output level may be respectively measured, the first output level for each of the optical receivers 113, 114, and 115 being a case in which the surface of one side is set as the detection surface 2b, the second output level for each of the optical receivers 113, 114, and 115 being a case in which the surface of the other side is set as the detection surface 2b. This case will be described as a second variation below.

In the second variation, the processing apparatus 130 may calculate the relevance ratio R1 by using the following formula (5), calculate the relevance ratio R2 by using the following formula (6), calculate the relevance ratio R3 by using the following formula (7), calculate the relevance ratio R4 by using the following formula (8), and determine a brand having the maximum value of R1×R4 or R2×R3 as the brand of the recording paper M.

$$R1 = \left(1 - \left|\frac{S1T - S11'}{S1T + S11'}\right|\right) \times \left(1 - \left|\frac{S2T - S21'}{S2T + S21'}\right|\right) \times \left(1 - \left|\frac{S3T - S31'}{S3T + S31'}\right|\right) \quad (5)$$

$$R2 = \left(1 - \left|\frac{S1B - S11'}{S1B + S11'}\right|\right) \times \left(1 - \left|\frac{S2B - S21'}{S2B + S21'}\right|\right) \times \left(1 - \left|\frac{S3B - S31'}{S3B + S31'}\right|\right) \quad (6)$$

In the formulae (5) and (6), in a case of setting one side to be the detection surface 2b, S11' indicates an average value of the output level of the light receiver 113, S21' indicates an average value of the output level of the light receiver 114, S31' indicates an average value of the output level of the light receiver 115, when the surface of the front side is set as the detection surface 2b. S11', S21', and S31' correspond to the first measurement data.

$$R3 = \left(1 - \left|\frac{S1T - S12'}{S1T + S12'}\right|\right) \times \left(1 - \left|\frac{S2T - S22'}{S2T + S22'}\right|\right) \times \left(1 - \left|\frac{S3T - S32'}{S3T + S32'}\right|\right) \quad (7)$$

$$R4 = \left(1 - \left|\frac{S1B - S12'}{S1B + S12'}\right|\right) \times \left(1 - \left|\frac{S2B - S22'}{S2B + S22'}\right|\right) \times \left(1 - \left|\frac{S3B - S32'}{S3B + S32'}\right|\right) \quad (8)$$

In the formulae (7) and (B), in a case of setting the other side to be the detection surface 2b, S12' indicates an average value of the output level of the light receiver 113, S22' indicates an average value of the output level of the light receiver 114, S32' indicates an average value of the output level of the light receiver 115, when the surface of the front side is set as the detection surface 2b. S12', S22', and S32' correspond to the second measurement data.

In the second variation, if R1×R4>R2×R3, it is determined that the other surface is the surface of the front side. If R1×R4<R2×R3, it is determined that the other surface is the surface of the back side.

Operations conducted by the operator will be described in the second variation.

1. Place the recording paper M of the differentiation target on the flat section 2a so that the surface of one side is set to be the detection surface 2b.
2. Pick up the sensor device 100 by hand, and put the sensor device 100 on the recording paper M.
3. Input a differentiation process request through the operation panel.

Figure 20:
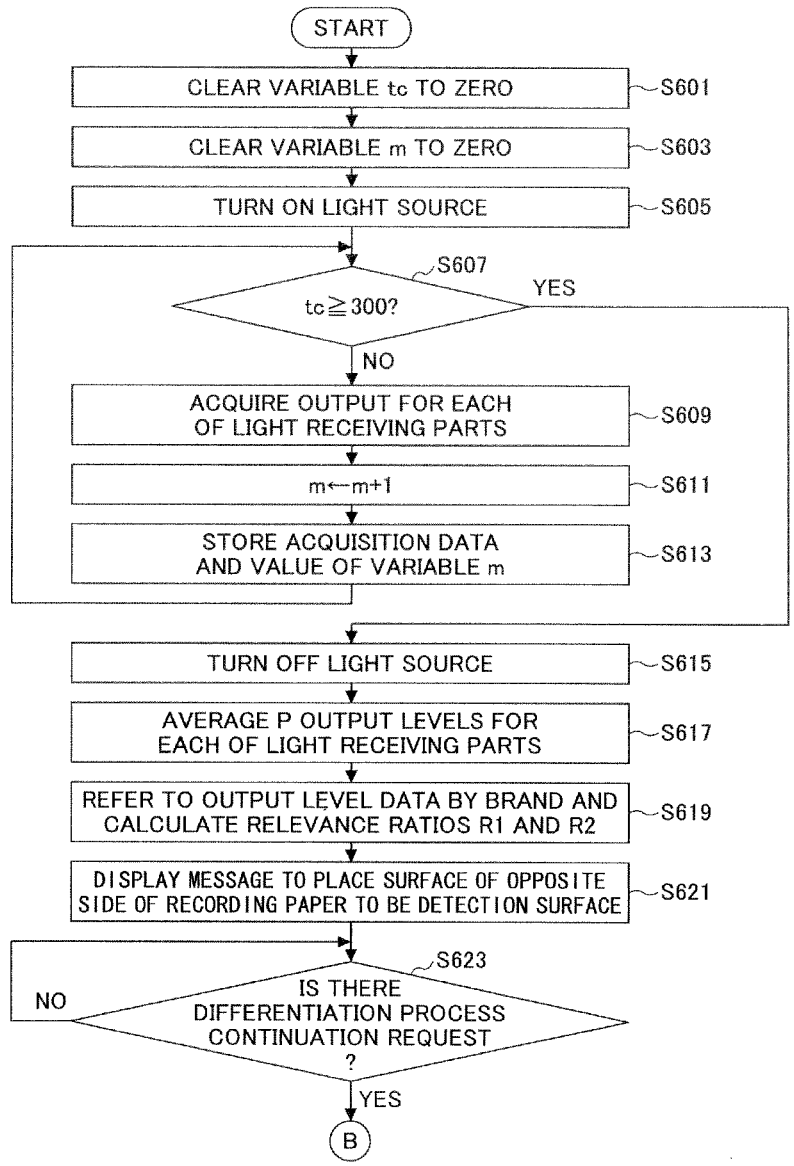
FIG. 20 is a flowchart for explaining a second variation of a brand differentiation process (part 1)
Figure 21:
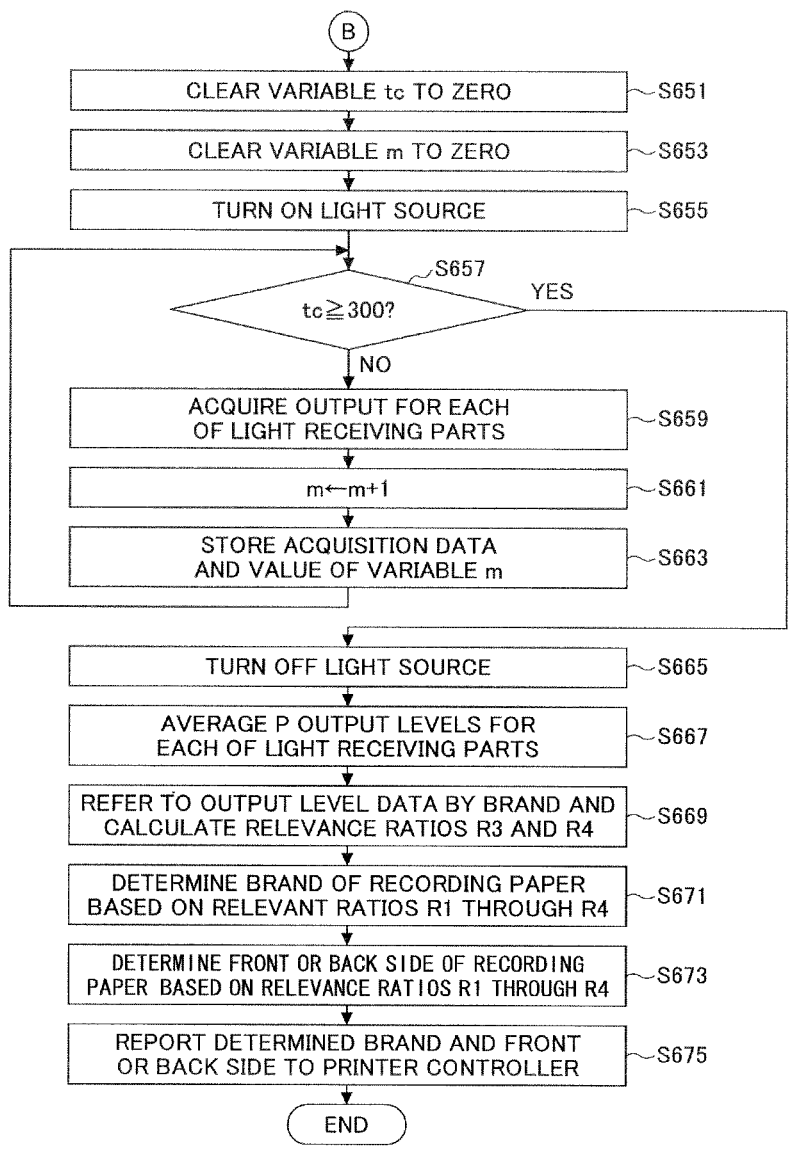
FIG. 21 is a flowchart for explaining the second variation of the brand differentiation process (part 2)

A flowchart for the second variation of the embodiment illustrated in FIG. 20 and FIG. 21 corresponds to a series of process algorithms executed by the CPU 131 of the processing apparatus 130 for the brand differentiation process.

First steps S601 through S617 are the same as steps S401 through S417 in the embodiment.

In next steps S619, the output level data T13 by brand stored in the ROM 132 is referred to. For each of the brands, the relevance ratio R1 is calculated by using the above formula (5), and the relevance ratio R2 is calculated by using the above formula (6).

In next step S621, a message is displayed at the display part of the operation panel via the printer controller 2090 to instruct the operator to place a surface of an opposite side of the recording paper M to be the detection surface 2b.

The operator sets a surface of the other side, which is the surface of the opposite side of the recording paper M, in accordance with the message, and inputs the differentiation process continuation request via the operation panel. The differentiation process continuation request is reported to the processing apparatus 130 of the sensor device 100 through the printer controller 2090 from the operation panel.

When the processing apparatus 130 receives the differentiation process continuation request, a determination in step S623 indicates positive, and the process advances to step S651.

The steps S651 through S667 are the same as steps S401 through S417 in the embodiment.

In next step S669, the output level data T13 by brand stored in the ROM 132 is referred to. For each of the brands, the relevance ratio R3 is calculated by using the formula (7), and the relevance ratio R4 is calculated by using the formula (8).

In next step S671, a brand having a maximum value of R1×R4 or R2×R3 is selected, and the selected brand is determined as the brand of the recording paper M.

In next step S673, based on the relevance ratios R1 through R4, it is determined whether the surface of one side is the surface of the back side. If R1×R4>R2×R3, it is determined that the surface of one side is the surface of the front side. If R1×R4<R2×R3, it is determined that the surface of one side is the surface of the back side.

In next step S675, the brand of the recording paper M and the front or back side are reported to the printer controller 2090. After that, the brand differentiation process is terminated.

Also, in the embodiment and the first and second variations of the embodiment, at least a part of the process by the CPU 131 in accordance with the program may be performed by hardware. Alternatively, the entire process may be performed by hardware.

Also, in the embodiment, a case, in which the light being illuminated onto the recording paper M is the S-polarization, is described above. However, the embodiment is not limited to this case. Alternatively, the light being illuminated onto the recording paper M may be the P-polarization. In this alternative case, instead of the polarization filter 116, a polarization filter for transmitting the S-polarization is used. The light receiver 114 receives the S-polarization component included in the internal reflected light.

Figure 22:
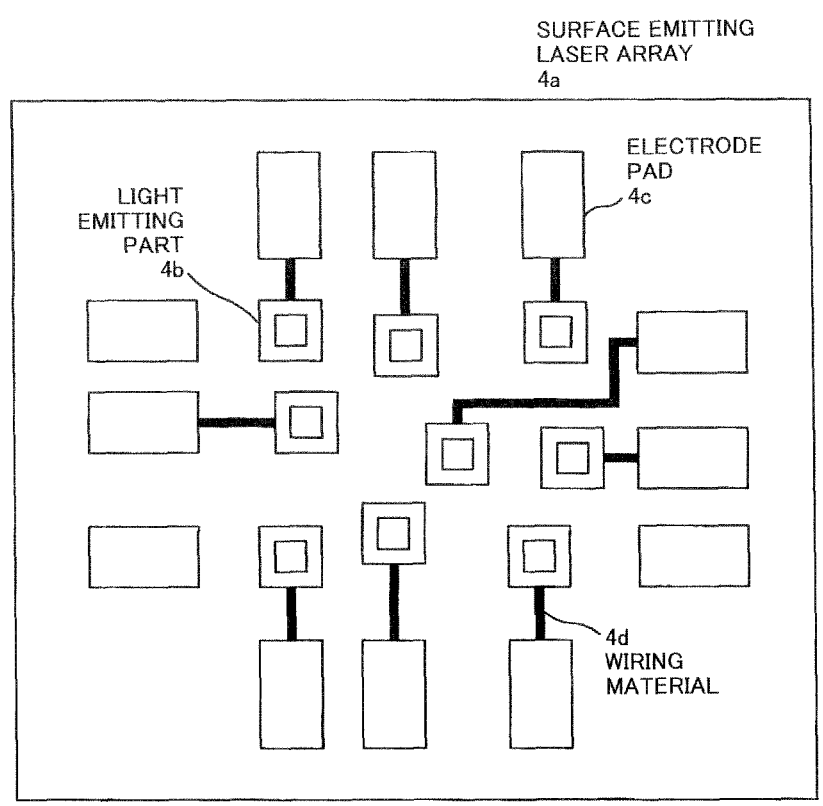
FIG. 22 is a diagram for explaining a variation of the surface emitting laser array.

Moreover, in the embodiment and the first and second variations, among the multiple light emitting parts 4b of the surface emitting laser array 9a, one or more intervals may be different from other intervals of the multiple light emitting parts 4b (see FIG. 22). That is, intervals of adjacent light emitting parts 4b may be different in distance.

Furthermore, in the embodiment and the first and second variations, a case in which the light source 111 includes nine light emitting parts 4b is described above. However, the embodiment and the first and second variations are not limited to this case.

Also, in the embodiment and the first and second variations, instead of the surface emitting laser array 4a, a laser diode may be used.

Figure 23:
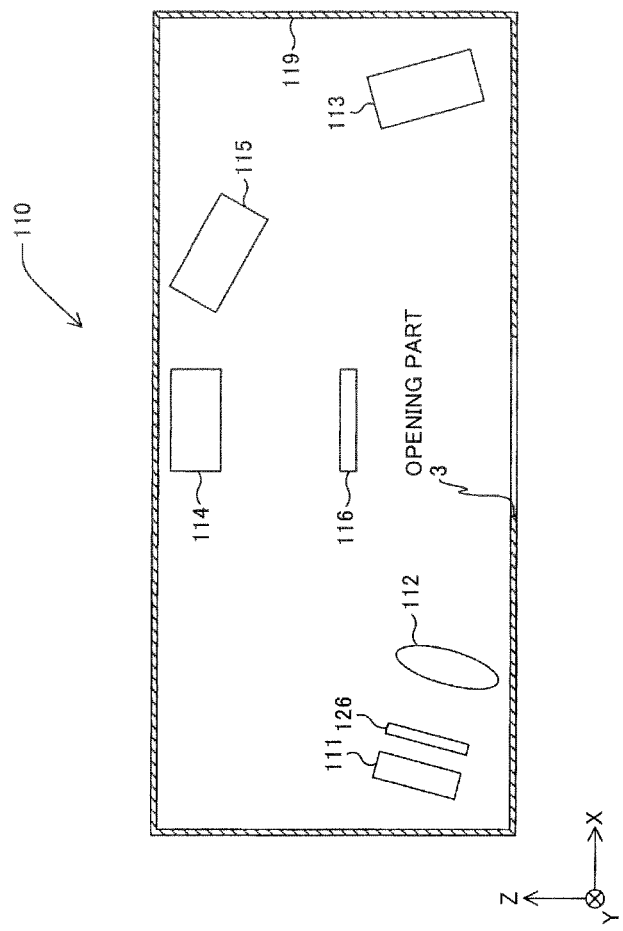
FIG. 23 is a diagram for explaining a first variation of an optical sensor.

Moreover, in the embodiment and the first and second variations, a case in which the linear polarization is emitted from the light source 111 is described. However, the embodiment and the first and second variations are not limited to this case. However, as depicted in FIG. 23, a polarization filter 126 is required to make the light emitted from the light source 111 be the S-polarization.

Furthermore, in the embodiment and the first and second variations, it is preferable to arrange a condensing lens in front of each of the optical receivers 113, 119, and 115. In this case, it is possible to reduce fluctuation of the light reception quantity by each of the optical receivers 113, 114, and 115.

Also, in the embodiment and the first and second variations, a case in which the brand differentiation process is conducted by the processing apparatus 130 is described above. The embodiment and the first and second variations are not limited to this case. For example, the brand differentiation process may be conducted by the printer controller 2090. In this case, the output level data T13 by brand may be stored in a ROM of the printer controller 2090.

Moreover, in the embodiment and the first and second variations, a case in which a light-on time of the light source 111 is 3 seconds in the brand differentiation process is described above. However, the embodiment and the first and second variations are not limited to this case. Also, the light-on time of the light source 111 may be set from the operation panel.

Furthermore, in the embodiment and the first and second variations, the sensor device 100 may include a start button of the brand differentiation process. In this case, the operator does not need to input the brand differentiation process request via the operation panel.

Also, in the embodiment and the first and second variations, the sensor device 100 may include a LED which is coupled with the light source 111. In this case, it is possible for the operator to visually know a light-on/light-off state of the light source 111.

Moreover, in the embodiment and the first and second variations, the sensor device 100 may include a display part. In this case, it is possible for the processing apparatus 130 to display a differentiation result at the display part.

Furthermore, in the embodiment and the first and second variations, a case in which the optical sensor 110 includes three optical receivers 113, 114, and 115 is described above. However, the embodiment and the first and second variations are not limited to this case. Depending on a required differentiation accuracy, for example, there may be two or four optical receivers in the optical sensor 110.

Figure 24:
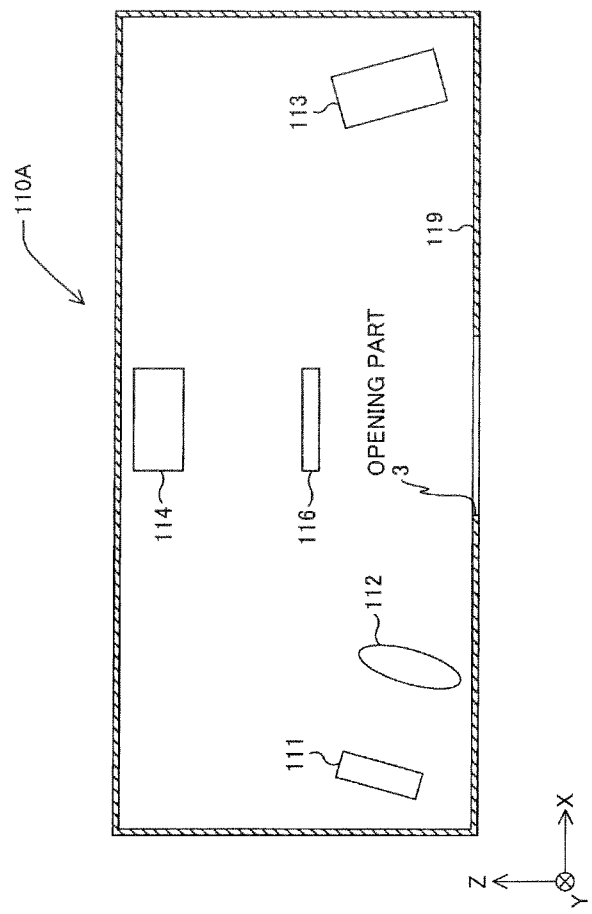
FIG. 24 is a diagram for explaining a second variation of the optical sensor.

FIG. 24 illustrates an optical sensor 110A excluding the optical receiver 115 of the optical sensor 110 in the embodiment and the first and second variations. In this case, the relevance ratio RT is calculated by using the following formula (9), and the relevance ratio RB is calculated by using the following formula (10).

$$RT = \left(1 - \left|\frac{S1T - S1'}{S1T + S1'}\right|\right) \times \left(1 - \left|\frac{S2T - S2'}{S2T + S2'}\right|\right) \quad (9)$$

$$RB = \left(1 - \left|\frac{S1B - S1'}{S1B + S1'}\right|\right) \times \left(1 - \left|\frac{S2B - S2'}{S2B + S2'}\right|\right) \quad (10)$$

Figure 25:
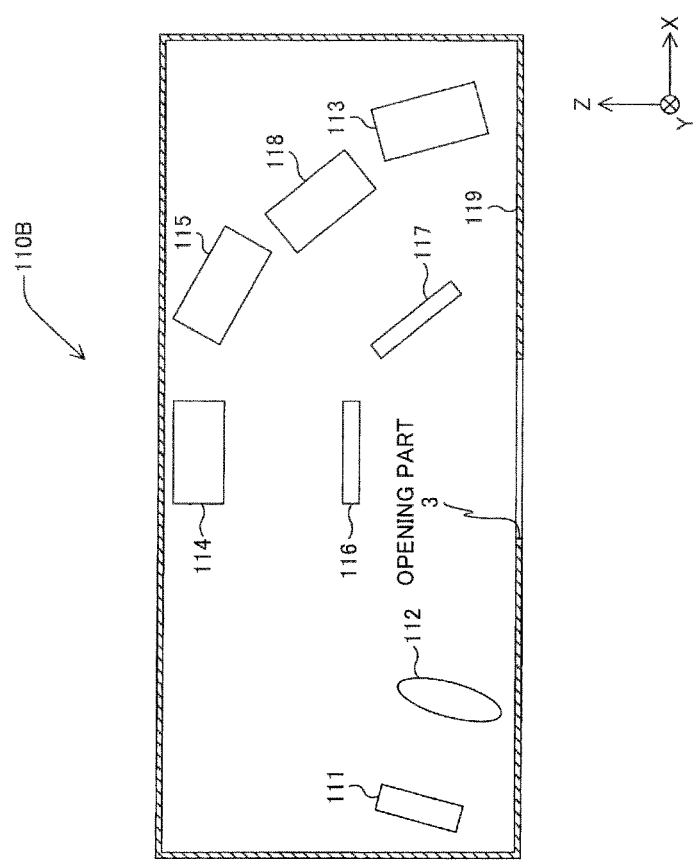
FIG. 25 is a diagram for explaining a third variation of the optical sensor.

Also, FIG. 25 illustrates an optical sensor 110B in which a polarization filter 117 and an optical receiver 118 are additionally provided to modify the optical sensor 110 in the embodiment and the first and second variations. The polarization filter 117 is arranged on a light path of the surface diffusion reflected light and the internal reflected light. The polarization filter 117 transmits the P-polarization component and blocks the S-polarization component. The optical receiver 118 is arranged on a light path of light passing through the polarization filter 117. The optical receiver 118 receives the P-polarization component included the internal reflected light. In this case, the relevance ratio RT is calculated by using the following formula (11), and the relevance ratio RB is calculated by using the following formula (12).

$$RT = \left(1 - \left|\frac{S1T - S1'}{S1T + S1'}\right|\right) \times \left(1 - \left|\frac{S2T - S2'}{S2T + S2'}\right|\right) \times \\ \left(1 - \left|\frac{S3T - S3'}{S3T + S3'}\right|\right) \times \left(1 - \left|\frac{S4T - S4'}{S4T + S4'}\right|\right) \quad (11)$$

$$RB = \left(1 - \left|\frac{S1B - S1'}{S1B + S1'}\right|\right) \times \left(1 - \left|\frac{S2B - S2'}{S2B + S2'}\right|\right) \times \\ \left(1 - \left|\frac{S3B - S3'}{S3B + S3'}\right|\right) \times \left(1 - \left|\frac{S4B - S4'}{S4B + S4'}\right|\right) \quad (12)$$

In the formulae (11) and (12), S4T represents the output level of the optical receiver 118 in a case of placing the surface of the front side as the detection surface 2b, S4B represents the output level of the optical receiver 118 in a case of placing the surface of the back side as the detection surface 2b, and S4' represents an average value of the output level of the optical receiver 118 in a case of emitting the light to the recording paper M of the differentiation subject.

In this case, output level data T26 by brand in FIG. 26 is referred to. Similar to the output level data T13 by brand in FIG. 13, the output level data T26 by brand correspond to a database including output data of multiple optical receivers 113, 114, 115, and 118 which are acquired beforehand in both cases of placing the surfaces of the front and back sides of the recording paper M as the detection surface 2b, regarding the recording papers M being different brands from each other in which each of the brands is known.

In the output level data T26 by brand, in a case in which the surface of the front side of the recording paper M is place as the detection surface 2b, S1T represents the output level of the optical receiver 113, S2T represents the output level of the optical receiver 114, S3T represents the output level of the optical receiver 115, and S4T represents the output level of the optical receiver 118. In a case in which the surface of the back side of the recording paper M is place as the detection surface 2b, S1B represents the output level of the optical receiver 113, S2B represents the output level of the optical receiver 114, S3B represents the output level of the optical receiver 115, and S4B represents the output level of the optical receiver 118. That is, S1T, S2T, S3T, and S4T correspond to first output data 26-1, and S1B, S2B, S3B, and S4B correspond to second output data 26-2.

Figure 27:
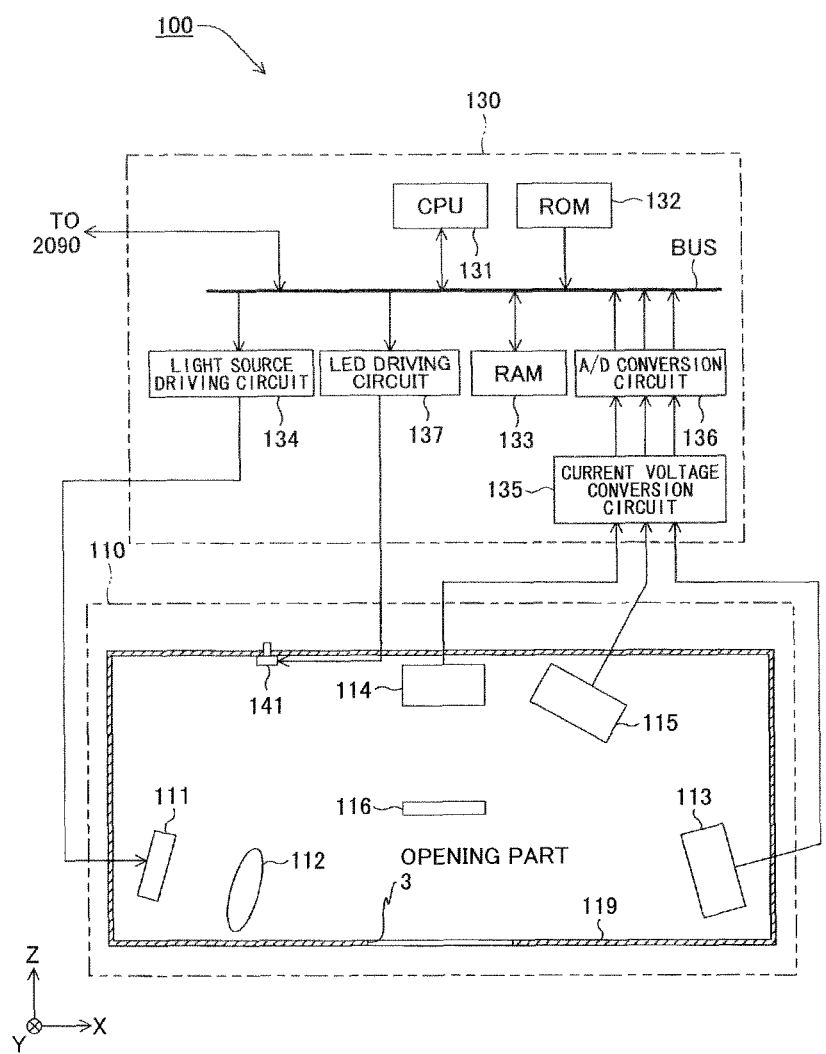
FIG. 27 is a diagram for explaining the first variation of the optical sensor.

Moreover, in the embodiment and the first and second variations, as illustrated in FIG. 27 as an example, in the camera obscure 119 of the sensor device 100, an LED 141 visible to the operator may be mounted, and a LED driving circuit 137 may be additionally provided to the processing apparatus 130. For example, the CPU 131 may turn on the LED 141 through the LED driving circuit 137 when the detection surface 2b is the surface of the back side. In a case in which the print condition is optimized for the front surface of the recording paper M for each of the brands in the image forming apparatus, when seeing light of the LED 141, the operator (the user) may reset the recording paper M so that the front surface is set to be printed. That is, by reporting the differentiation result of the front or back side of the recording paper M to the operator (the user), it is possible to urge the operator to set the recording paper M so that a surface suitable for high quality printing is to be printed. Instead of the LED 141, another luminous body may be used.

Figure 28:
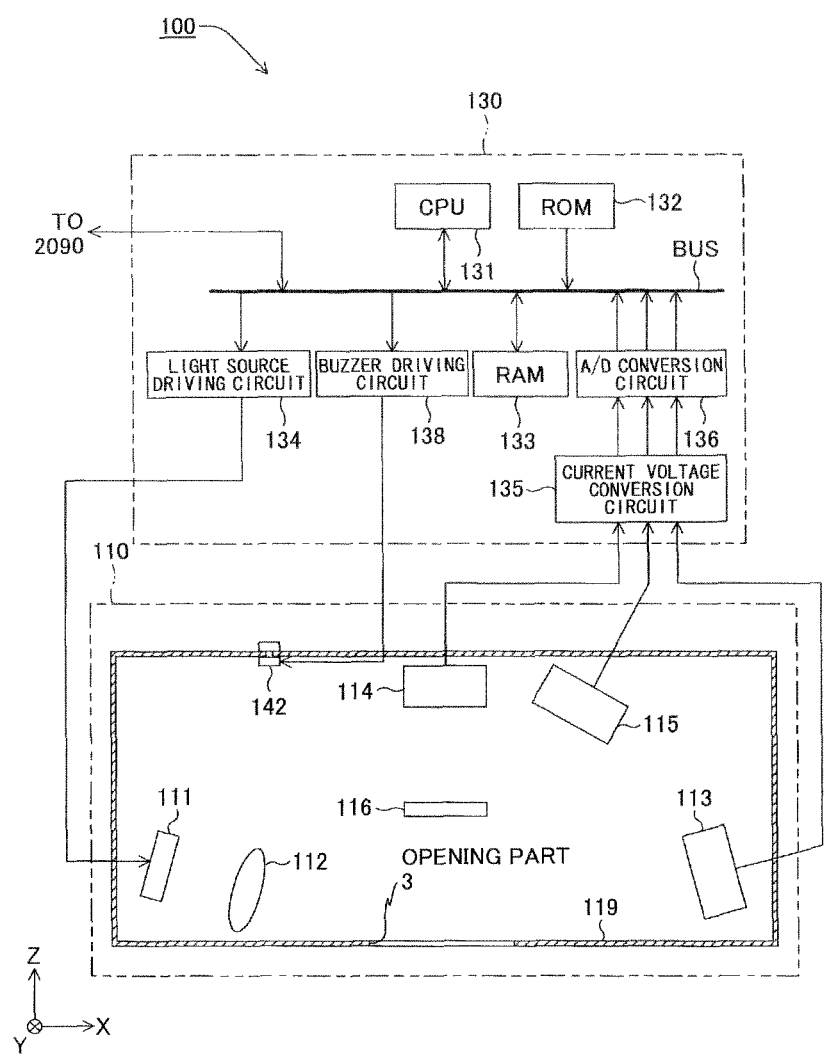
FIG. 28 is a diagram for explaining the second variation of the optical sensor.

Furthermore, in the embodiment and the first and second variations, as illustrated in FIG. 28 as an example, in the camera obscure 119 of the sensor device 100, a buzzer 142, which is possible for the operator to hear, may be mounted, and a buzzer driving circuit 138 may be additionally provided to the processing apparatus 130. For example, the CPU 131 may sound the buzzer 142 through the buzzer driving circuit 138 when the detection surface 2b is the surface of the back side. In a case in which the print condition is optimized for the front surface of the recording paper M for each of the brands in the image forming apparatus, when the operator (the user) hears the sound of the buzzer 142, the operator (the user) may reset the recording paper M so that the front surface is set to be printed. Instead of the buzzer 142, another sounding body may be used.

Also, the LED 141 and the buzzer 142 may be mounted to the operation panel. In brief, the differentiation result of the front or back side of the recording paper M (paper sheet) may be reported to the operator (the user).

Moreover, in the embodiment and the first and second variations, a case of one paper feeding tray is described above. The embodiment and the first and second variations are not limited to this case. There may be multiple paper feeding trays.

Moreover, the object to be differentiated by the sensor device 100 is not limited to the recording paper M.

Furthermore, in the embodiment and the first and second variations, a case of the color printer 2000 as the image forming apparatus is described above. However, the embodiment and the first and second variations are not limited to this case. For example, a laser printer for forming a black and white image may be used as the image forming apparatus. Also, an image forming apparatus other than a printer, for example, a copier, a facsimile machine, or a multifunction peripheral integrating these functions may be used.

Also, in the embodiment and the first and second variations, a case in which the image forming apparatus includes four photosensitive drums 203D is described above. However, the embodiment and the first and second variations are not limited to this case. For example, a printer including five photosensitive drums may be used.

Moreover, in the embodiment and the first and second variations, the image forming apparatus, in which the toner images are transferred onto the recording paper M from the photosensitive drums 2030 via the transfer belt 2040, is described above. However, the embodiment and the first and second variations are not limited to this image forming apparatus. An image forming apparatus may be one in which the toner images are directly transferred from the photosensitive drums 2030 to the recording paper M.

Accordingly, at least one embodiment provides a sensor device and an image forming apparatus which determine the type of the object at higher precision with the simple configuration.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority or inferiority of the invention. Although the embodiment of the present invention has been described in detail, it should be understood that various changes, substitutions, and alterations could be made hereto without departing from the spirit and scope of the invention.

This patent application is based on Japanese Priority Patent Applications No. 2013-143136 filed on Jul. 9, 2013 and No. 2014-059385 filed on Mar. 24, 2014, the entire contents of which are hereby incorporated herein by reference.

What is claimed is:

1. A sensor device comprising:
 a light source which emits light of a linear polarization having a first polarization direction toward a detection surface of an object;
 an optical detection system including
  an optical element which is arranged on a first light path of the light undergoing a diffusion reflection at the object in an incident surface with respect to the detection surface of the light emitted from the light source, and which transmits a linear polarization component of a second polarization direction orthogonal to the first polarization direction,
  a first optical detector which is arranged on a second light path of the light undergoing a regular reflection; and
  a second optical detector which receives the light passing through the optical element;
 a database including, with respect to multiple different types of first objects,
  a first output data which are output data of the optical system acquired beforehand for each of the first objects in a case in which a surface of one side of the first object is set as the detection surface; and
  a second output data which are output data of the optical detection system acquired beforehand for each of the first objects in a case in which a surface of an other side opposite to the one side of the first object is set as the detection surface; and
 a processing apparatus configured to match measurement data with the database, the measurement data being the output data of the optical detection system which is acquired with respect to a second object, and to determine a type of the second object.

2. The sensor device as claimed in claim 1, wherein
 the measurement data are the output data of the optical detection system when one surface of the second object is set as the detection surface; and
 the processing apparatus calculates a first relevance ratio and a second relevance ratio, and determines the type of the second object based on the first relevance ratio and the second relevance ratio, wherein the first relevance ratio represents a matching degree between the measurement data and the first output data included in the database related to the multiple different types of first objects, and the second relevance ratio represents a matching degree between the measurement data and the second output data included in the database related to the multiple different types of first objects.

3. The sensor device as claimed in claim 2, wherein the processing apparatus further determines based on the first relevance ratio and the second relevance ratio whether the one surface is a surface of the one side of the second object or a surface of the other side of the second object.

4. The sensor device as claimed in claim 1, wherein the measurement data include first measurement data being output data of the optical detection system in a case in which the surface of the one side of the second object is set as the detection surface, and second measure data being output data of the optical detection system in a case in which the surface of the other side of the second object is set as the detection surface, and the processing apparatus calculates a first relevance ratio and a second relevance ratio, and determines the type of the second object based on the first relevance ratio and the second relevance ratio, wherein the first relevance ratio represents a matching degree between the first measurement data and the first output data included in the database, and the second relevance ratio represents the matching degree between the second measurement data and the second output data included in the database, wherein the database is related to the multiple different types of first objects.

5. The sensor device as claimed in claim 1, wherein the measurement data includes first measurement data being output data of the optical detection system in a case in which a first surface of the second object is set as the detection surface, and second measure data being output data of the optical detection system in a case in which a surface of an opposite side to the first surface of the second object is set as the detection surface, and the processing apparatus calculates a first relevance ratio, a second relevance ratio, a third relevance ratio, and a fourth relevance ratio, and determines the type of the second object based on the first relevance ratio, the second relevance ratio, the third relevance ratio, and the fourth relevance ratio, wherein the first relevance ratio represents a matching degree between the first measurement data and the first output data included in the database, the second relevance ratio represents the matching degree between the first measurement data and the second output data included in the database, the third relevance ratio represents the matching degree between the second measurement data and the first output data included in the database, and the fourth relevance ratio represents the matching degree between the second measurement data and the second output data included in the database.

6. The sensor device as claimed in claim 5, wherein the processing apparatus further determines based on the first relevance ratio, the second relevance ratio, the third relevance ratio, and the fourth relevance ratio whether the first surface is the surface of the one side or the surface of the other side.

7. The sensor device as claimed in claim 1, further comprising a report part configured to report to a user whether the detection surface is the surface of the one side of the second object or the surface of the other side of the second object.

8. The sensor device as claimed in claim 1, wherein the processing apparatus emits light from the light source to multiple locations on the detection surface, and acquires multiple sets of the output data from the first optical detector and the second optical detector.

9. The sensor device as claimed in claim 1, wherein the optical detection system includes a third optical detector which is arranged on the light path of the light undergoing the diffusion reflection from the object in the incident surface.

10. The sensor device as claimed in claim 1, wherein the light source includes a surface emitting laser array.

11. An image forming apparatus for forming an image on a recording medium, the image forming apparatus comprising:

a sensor device as claimed in claim 1 in which the recording medium is the object; and an adjustment device configured to adjust an image formation condition based on a differentiation result of the sensor device.

12. The image forming apparatus as claimed in claim 11, wherein the differentiation result of the sensor device includes information pertaining to a type of the recording medium, or the type and a front or back side of the recording medium.

* * * * *